United States Patent
Halder et al.

(10) Patent No.: US 10,981,925 B2
(45) Date of Patent: Apr. 20, 2021

(54) SELF-EXFOLIATED TRIAZOLE-TRIFORMYL PHLOROGLUCINOL BASED COVALENT ORGANIC NANOSHEETS FOR HIGH AND REVERSIBLE LITHIUM ION STORAGE

(71) Applicant: INDIAN INSTITUTE SCIENCE EDUCATION AND RESEARCH, Pune (IN)

(72) Inventors: Sattwick Halder, Pune (IN); Kingshuk Roy, Pune (IN); Shyamapada Nandi, Pune (IN); Ramanathan Vaidhyanathan, Chennai (IN)

( * ) Notice: Subject to any disclaimer, the term of this patent is extended or adjusted under 35 U.S.C. 154(b) by 0 days.

(21) Appl. No.: 16/700,481

(22) Filed: Dec. 2, 2019

(65) Prior Publication Data

US 2020/0123169 A1 Apr. 23, 2020

Related U.S. Application Data

(63) Continuation of application No. PCT/IN2018/050351, filed on May 31, 2018.

(30) Foreign Application Priority Data

Jun. 2, 2017 (IN) .............................. 201721019419

(51) Int. Cl.
*C07D 487/22* (2006.01)
*H01M 4/60* (2006.01)
*H01M 10/0525* (2010.01)
*B82Y 30/00* (2011.01)
*C07C 47/565* (2006.01)
*C07D 249/14* (2006.01)

(52) U.S. Cl.
CPC .......... *C07D 487/22* (2013.01); *H01M 4/608* (2013.01); *H01M 10/0525* (2013.01); *B82Y 30/00* (2013.01)

(58) Field of Classification Search
CPC ... C07D 487/22; C07D 249/14; H01M 4/608; H01M 10/0525; B82Y 30/00; C07C 47/565; Y02E 60/10
See application file for complete search history.

(56) References Cited

PUBLICATIONS

Chong, J.H., "Highly stable keto-enamine salicylideneanilines." Organic letters 5.21 (2003): 3823-3826.*

\* cited by examiner

*Primary Examiner* — John M Mauro
(74) *Attorney, Agent, or Firm* — Kramer Amado

(57) ABSTRACT

The invention discloses covalent organic nanosheets (CONs) made of triazole based diamine and triformyl phloroglucinol. The 2D structure of these nanosheets enables their facile amalgamation as an anodic material in a coin cell battery, which exhibits exceptionally high specific capacity of ~720 mAh/g at a current density of 100 mA/g.

10 Claims, 28 Drawing Sheets

Hexagonal geometry of the IISERP-CON1

Monomer of the IISERP-CON1

SELF-EXFOLIATED TRIAZOLE-TRIFORMYL PHLOROGLUCINOL BASED COVALENT ORGANIC NANOSHEETS FOR HIGH AND REVERSIBLE LITHIUM ION STORAGE

RELATED APPLICATIONS

This application is a continuation of International Patent Application No. PCT/IN2018/050351, filed May 31, 2018, and published as International Patent Publication No. WO 2018/220650 on Dec. 6, 2018, which claims priority to Indian Patent Application 201721019419, filed Jun. 2, 2017. Each of these prior patent documents is incorporated by reference herein in its entirety.

FIELD OF INVENTION

The present invention relates to covalent organic nanosheets (CONs), methods of making such nanosheets, and devices comprising such nanosheets. More particularly, the invention relates to covalent organic nanosheets (CONs) made of triazole based diamine and triformyl phloroglucinol. The 2D structure of these nanosheets enables their facile amalgamation as an anodic material in a coin cell battery, which exhibits exceptionally high specific capacity of ~720 mAh/g at a current density of 100 mA/g.

BACKGROUND AND PRIOR ART

Covalent organic frameworks (COFs) owing to their modular structure and ordered porosity can serve as chemically tunable supports. Typically Lithium ion batteries (LIB) are built from Graphite and $LiCoO_2$. A common feature of these anodic and cathodic materials is their 2D structure. Since their initial discovery, many 2D materials with comparable layered structure have been explored as Li insertion/de-insertion substrate.

Some of the highly desirable characteristics of a superior electrode material include their moderate to high surface area to ensure maximum charge storage per unit area, and the other is the hierarchical porosity rendering facile access for favourable kinetics. One of the key attributes of graphite which has made it historically most utilized storage material is its ability to exfoliate. Exfoliation-assisted surface area/porosity enhancement and adsorption site creation is facile in organic substrates such as graphene, $MoS_2$, CNT or other carbonaceous structures, which makes them components of top-performing Li and Na storage materials for batteries. In this regard, Covalent Organic Frameworks could have much more to offer as they are typically built with pre-designed cross-linking units to assist construction of extended/periodic hexagonal or square-grid layers. Also, their C/N or C/B, or in general, the atom1/atom2 ratio can be controlled with stoichiometric exactness and the chemical function (e.g. Nitrogen: pyridyl vs. triazine vs. Schiff) which can be modified.

Another feature of relevance for developing as electrode material comes from the type of inter-layer interactions they possess. Typically, the COF layers are held together by interlayer π-π interactions or in special cases via additional hydrogen bonding. In their optimized structure, the interlayer separations typically fall in the range of 3.2 to 4.5 A. Moreover, unlike graphite, the layers of COF are not built from fused aromatic rings. Hence, the interaction forces are optimal for holding them together, but more importantly to support facile exfoliation without losing the overall structure. Particularly, the COFs formed by imine linkages are amenable to exfoliate into nanosheets. This exfoliation can have marked consequence in ion storage (S. Wang, Lijiang Wang, Kai Zhang, Zhiqiang Zhu, Zhanliang Tao, and Jun Chen, Nano Lett., 2013, 13, 4404-4409. (b) Oscar A. Vargas C., Álvaro Caballero and Julian Morales, Nanoscale, 2012, 4, 2083-2092).

Also, in COFs, the building units are longer and contain flexible bonds. Therefore the layers of COF show a by demand structural rearrangement which facilitates accommodating the extra-framework species, be it ions or nanoparticles. This flexibility and tunability has made COFs find its use in gas storage, hydrogen evolution, proton conduction, quantum sieving, photoconductivity, catalysis, and even in self-cleaning superhydrophobic surfaces and sensing. Conducting and semi-conducting COFs built from components rich in electronic character (conjugated π-clouds, donor-acceptor nodes or high polarizing moieties) have been used as electrodes or electrolytes.

The research on lithium storage using several carbon rich materials, polymers and classical inorganic oxides, sulfides have been known for several decades. Lithium insertion in Nitrogen-doped graphenes is also known. In comparison, less is known about utilizing covalent organic frameworks for lithium ion storage. As an effective approach, Yuliang Li et al. designed a porphyrin-thiophene-based conjugated COF with enhanced intrinsic electronic conductivity and demonstrated high specific capacity of up to 666 mAh/g, but this specific capacity was seen to drop significantly with increasing current density. Also, there are some interesting theoretical studies focused on the inclusion of Li into the frameworks of COFs, all of which point at the Li ions being bound to the hydrocarbon backbone, more precisely, to the aromatic rings forming the COF that can facilitate chemical interactions with Li.

Similarly, $Fe_2O_3$ supported on nanosheets of graphene shows high anode activity (1355 and 982 mAh/g for charge and discharge cycles, respectively), arising from the redox reactivity at the iron center. However, one serious problem involved in these redox active systems is that upon cycling they tend to drop in performance owing to some irreversible reactions between the Li and the substrate. At higher current densities such undesirable irreversible reactions become more frequent and are typically characterized by their low columbic efficiency. Other carbonaceous support stabilized iron based anodes are also plagued by similar issues. So relatively less reactive (Lewis basic/acidic) and neutral systems could be advantageous when it comes to obtaining prolonged cycle life.

Covalent Organic Nanosheets (CONs) have tunable modular structure and high surface areas. Covalent organic frameworks under hydro/solvothermal conditions can grow into self-exfoliated nanosheets. Their graphene/graphite resembling micro-texture/nano-structure makes them suitable for electrochemical applications. The covalent organic nanosheet (CONs) is a disordered derivative of a COF, and this brings some advantages. While the highly ordered porous structure of a COF could bring advantage kinetics, confinement and accessibility; converting them into relatively more disordered nanosheets could be profitable for a different reason. The disordered carbon nanostructures can in many cases display practical capacities higher than even the theoretical capacity of graphite. Partly this is due to their ability to generate carbons of higher oxidation state under the electrochemical force provided during the Li insertion. Crucially, such reactions are reversible. This could mean that CONs can present chemical and structural features aptly suited for Li insertion under the electrochemical potential of a battery.

Under the above background, it has become an objective of the present invention to provide a novel COF which can be self-exfoliated into covalent organic nanosheets (CONs) with exceptional stability and high porosity and thus most suited for Li ion insertion.

SUMMARY OF THE INVENTION

In line with the above objective, the present invention provides novel self-exfoliated covalent organic frameworks (COFs) derived covalent organic nanosheets (CONs) with nanopores sumptuously lined by mildly binding triazole and phloroglucinol units. Precisely, the present invention provides self-exfoliated covalent organic framework derived nanosheets (CONs) with good stability and high porosity comprising plurality of 3,5-diaminotriazole units and plurality of triformyl phloroglucinol units, in extended layered covalent framework wherein, the triazole based diamine units are mildly bonded to the triformyl phloroglucinol units. The novel COF according to the invention during synthesis has grown into self-exfoliated covalent organic nanosheets (CONs), herein after referred as IISERP-CON1, with exceptional stability and high porosity that can be attributed to its keto-enol tautomerism stabilized framework. Accordingly, the present invention provides a novel CONs (COF-derived nanosheets) based on 3,5-diaminotriazole and triformyl phloroglucinol with exceptional stability and high porosity.

3,5-diaminotriazole also referred as 2,4-diaminotriazole or 3,5-diamino-1,2,4-triazole in the description, may be considered as synonymous with each other. Similarly, 'triazole' wherever appeared in the description needs to be referred as '3,5-diaminotriazole' unless specifically stated otherwise and the 'trialdehyde' or 'phloroglucinol' needs to be referred as 'triformyl phloroglucinol', for the purpose of the present invention.

In another aspect, the novel CONs of the present invention is prepared by reacting a trialdehyde with 2,4-diaminotriazole (3,5-diaminotriazole) in dioxane in presence of dimethylacetamide and mesitylene under stirring. The trialdehyde as used herein is triformyl phloroglucinol. The presence of triazole rings in the CON brings sufficient flexibility to the framework.

In yet another aspect, realizing the potential of such CONs for Li insertion-deinsertion, the present inventors have investigated the advantages it brings as anode material when used in a device. The device according to the invention is selected from the group consisting of solar cells, batteries, capacitors etc.

Accordingly, the invention provides a device comprising novel self-exfoliated covalent organic frameworks (COFs) derived covalent organic nanosheets (CONs). In an exemplified embodiment, the device is Li batteries. The 2D structure of the nanosheets of the present CONs exhibits high specific capacity ~720 mAh/g at a high current density of 100 mA/g, when used as an anode in coin-cell anode, which to the best of inventor's knowledge is the highest reported capacity among all the self-standing non-Graphenic organic materials reported till date. Further, these nanosheets display only little drop (~150 mAh/g) in specific capacity even at current densities as high as 2 A/g. Importantly, increasing the current density from 100 mA/g to 1 A/g causes the specific capacity to drop only by 20%, which is lowest among all high-performing anodic covalent organic frameworks.

Moreover, when these nanosheets are used as anode material in Li battery, the cell retains this high specific capacity even after 100 cycles. Molecular Dynamics/DFT coupled with analytical studies display the optimal structure and interaction the COF has with the Li species, which explains its high-performance.

The fibrous texture of the nanosheets of the invention enables their facile amalgamation as a coin-cell anode, which exhibits exceptionally high specific capacity of ~720 mAh/g at a current density of 100 mA/g. This capacity is maintained even after 100 cycles. From cyclic voltammetry, using Cottrell equation, the inventors have identified that the majority of the Li insertion is due to an ultra-fast diffusion controlled intercalation process (Diffusion coefficient, $D_{Li+}$, =5.48×10-11 cm2s-1). The absence of any strong Li-framework bonds in the simulated structure of Li@CON further explains this facile and reversible Li intercalation. This is verified by chemical analysis too. Interestingly, a discrete monomer of the CON constructed from triformyl phloroglucinol+3-aminotriazole (FIG. 6) shows 4 times lowered specific capacity (140 mAh/g @ 50 mA/g) and no sign of Li-intercalation, which reveals that the extended layered covalent framework of the CON is crucial to the intercalation-assisted conductivity. Furthermore, the electron density/electrostatic potentials mapped using DFT calculations suggests substantial electronic driving force for the intercalation of Li into the CON. The IISERP-CON1 provided according to the invention have optimal structure, functionality and electronics for reversible Li insertion making these designer covalent organic nanosheets as an excellent choice for anode material for lithium batteries.

DESCRIPTION OF DRAWINGS

The patent or application file contains at least one drawing executed in color. Copies of this patent or patent application publication with color drawing(s) will be provided by the Office upon request and payment of the necessary fee.

Note: No significant change of CV profile peak position was obtained. That suggests no degradation of electrode was happened even after $100^{th}$ cycle corresponding to no capacity loss.

Figure 16:
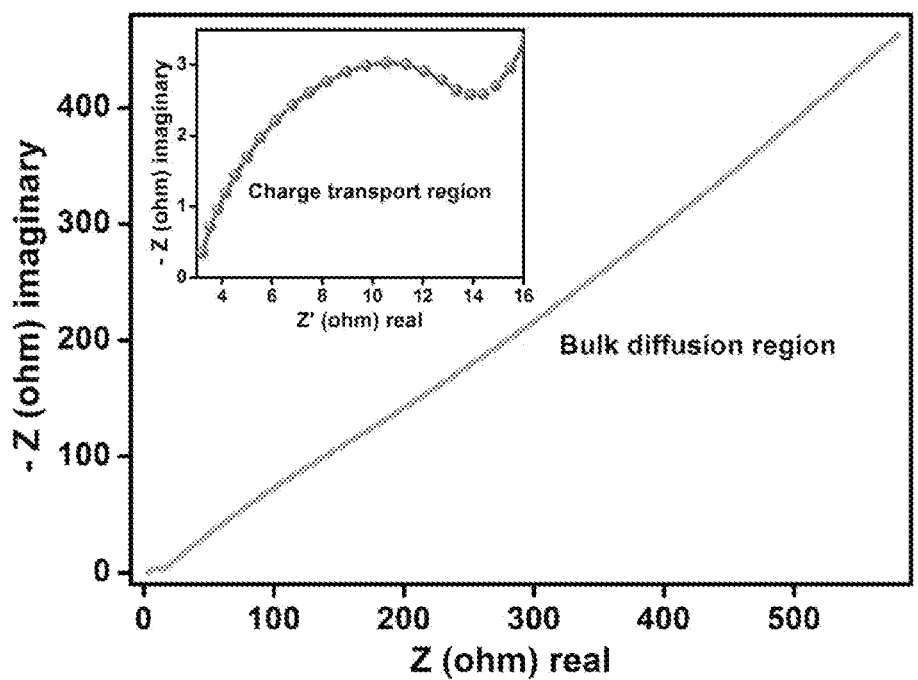

FIG. 16: Nyquist plots of IISER-CON1 electrode after completion of SEI formation after 100 cycles (orange curve).

Figure 17:
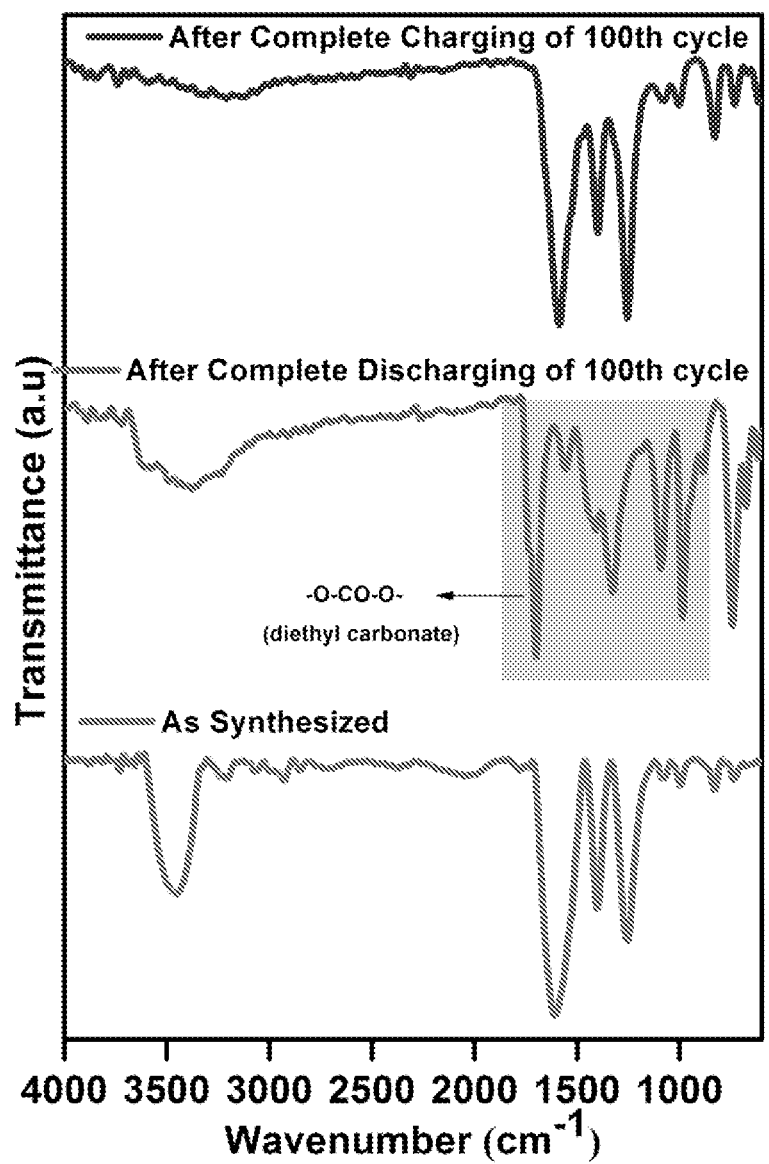

FIG. 17: FT-IR spectra of IISERP-CON1 made electrode before charging-discharging in comparison with after 100 cycle charging-discharging. There was no significant change observed in the characteristic peaks (carbonyl (—C═O) at 1665 cm$^{-1}$; —NH str. and —OH str. (~3454 cm-1); —C═N str. (1604 cm$^{-1}$); —C═N (triazolic) str. (~1401 cm-1) and C—N str. (~1256 cm-1) bands.

Figure 18:
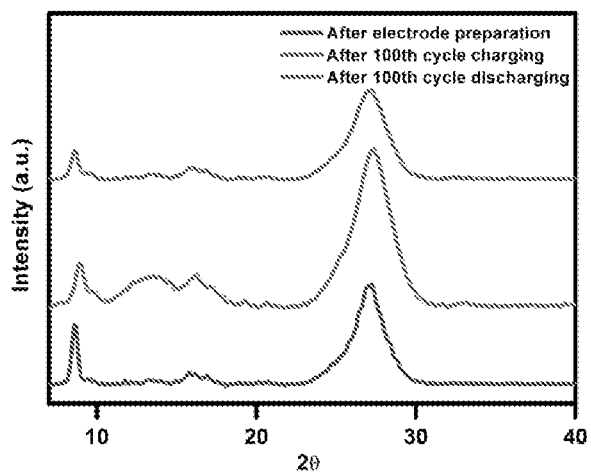

FIG. 18: PXRD pattern of IISERP-CON1 made electrode without any conducting carbon using before and after 100th cycle charge-discharge. The noticeable hump at ~2θ=12-14° is due to the lithiation and as can be seen, it disappears upon discharging.

Figure 19:
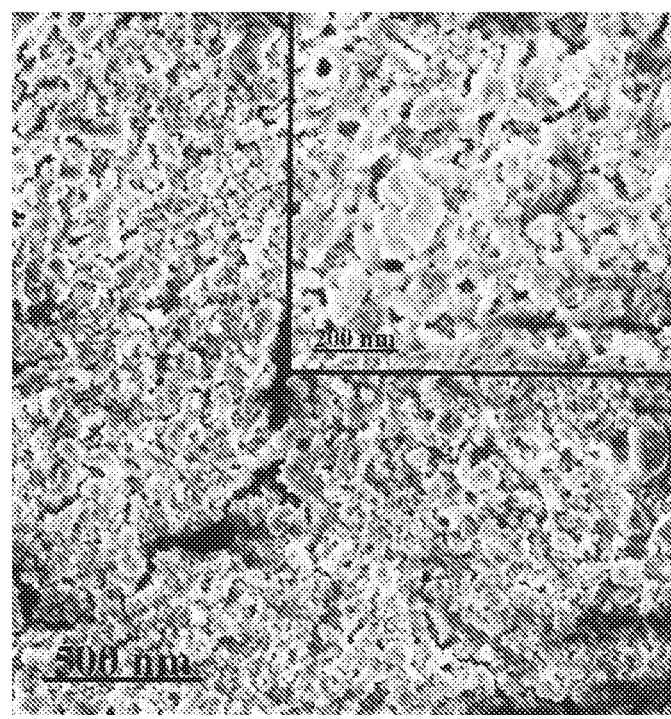

FIG. 19: FE-SEM image in different magnification after 100th cycle discharging. There is no noticeable agrregation between particles or growth into larger particles via Ostwald ripening.

Figure 20A:
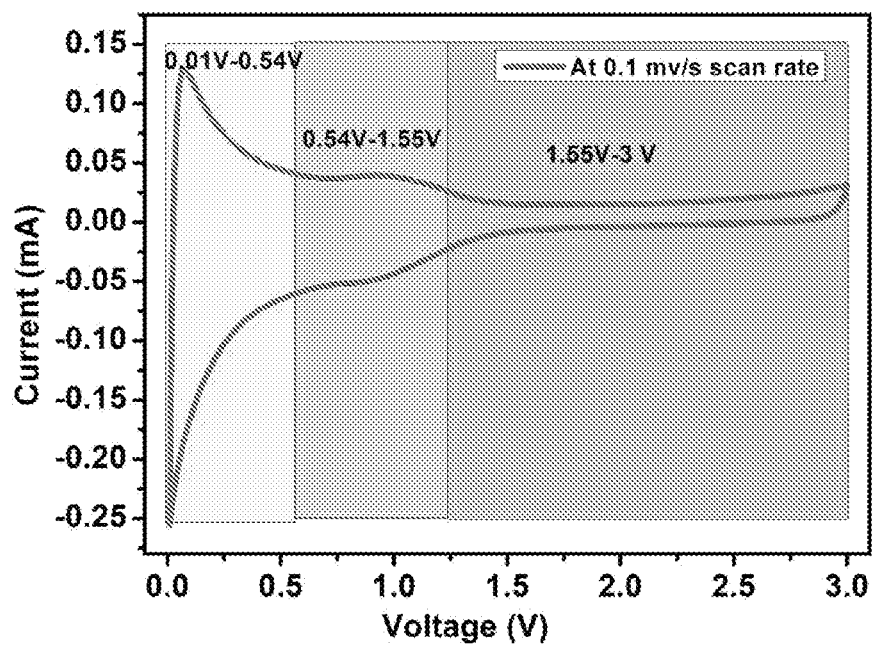
Figure 20B:
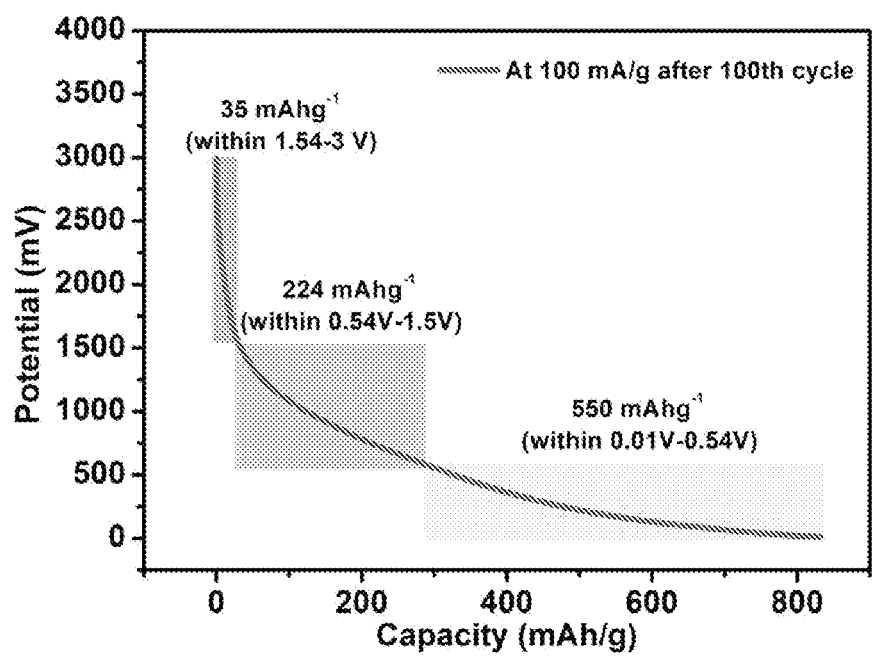

FIG. 20A shows different potential region of CV for surface activity (chemical reaction) and diffusion activity (intercalation). 0.01-0.54 V mainly responsible for intercalation of lithium and from 0.54-1.55V for chemical reaction with functional group. FIG. 20B shows potential vs capacity plot at 100 mAg$^{-1}$ for $100^{th}$ cycle. Same potential region obtained from CV and capacity contribution in each of those region was shown separately. Number of Lithium insertion contribution for capacity achievement in different potential region was calculated from the following calculation.

Calculation of lithium concentration in the Li@CON from the specific capacity:

1 mAh=3.6 C=2.2×10^19 no of electron or Li$^+$.

Here, for the IISERP-CON1 based coin-cell we observed a specific capacity of 550 mAhg$^{-1}$ in the potential region of 0.01-0.5V (This potential window represents the intercalation region observed in the CV).

This would yield the number of Li$^+$ ion=2.2×10^19× 550=1210×10^19.

Thus, the specific capacity of 550 mAhg$^{-1}$ is realized from 1210×10^19 no of Li$^+$ (assuming they are the sole charge carriers).

The calculated molecular weight of the IISERP-CON1 is 610 g/mol.

The weight for unit cell of the IISERP-CON1 is 610/(6.023× 10^23) g

Considering that for 1 g of the CON, the number of Li+ ion calculated is 1210×10^19=># of Li+ per unit cell=1210× 10^19×610/(6.023×10^23)=12.

Similarly, the second oxidation peak in the CV occurs in the potential window of 0.5-1.54V, and the specific capacity in this region is observed to be 224 mAhg$^{-1}$.

This now can be attributed to about 4 Li$^+$ per unit cell.

So, in total there are 16 Li$^+$ ions/unit cell of IISERP-CON1 involved in the insertion-deinsertion process giving rise to the overall specific capacity of 774 mAhg$^{-1}$.

Figure 21:
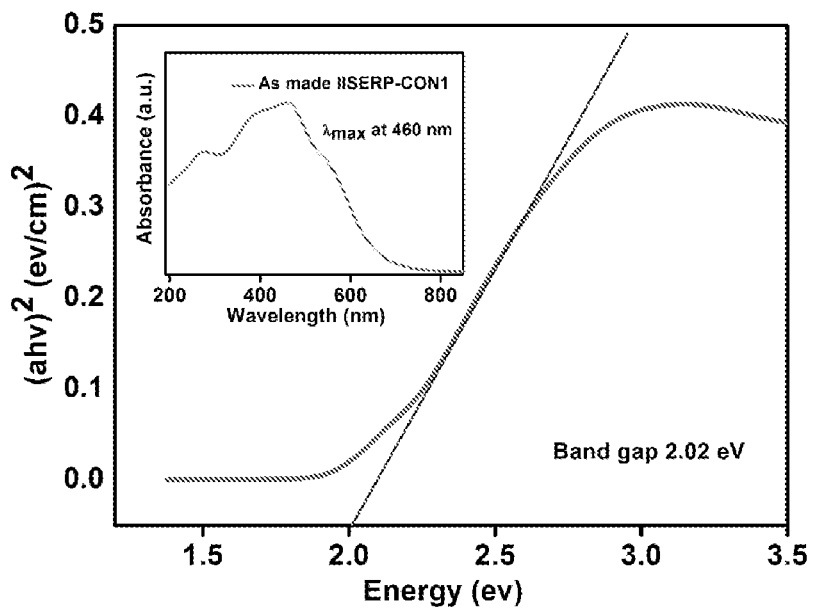

FIG. 21: Tauc plot of IISERP-CON1. Tangent of this plot gives 2.02 eV band gap. Inset solid state UV-visible spectra having maximum wavelength at 460 nm.

Figure 22:
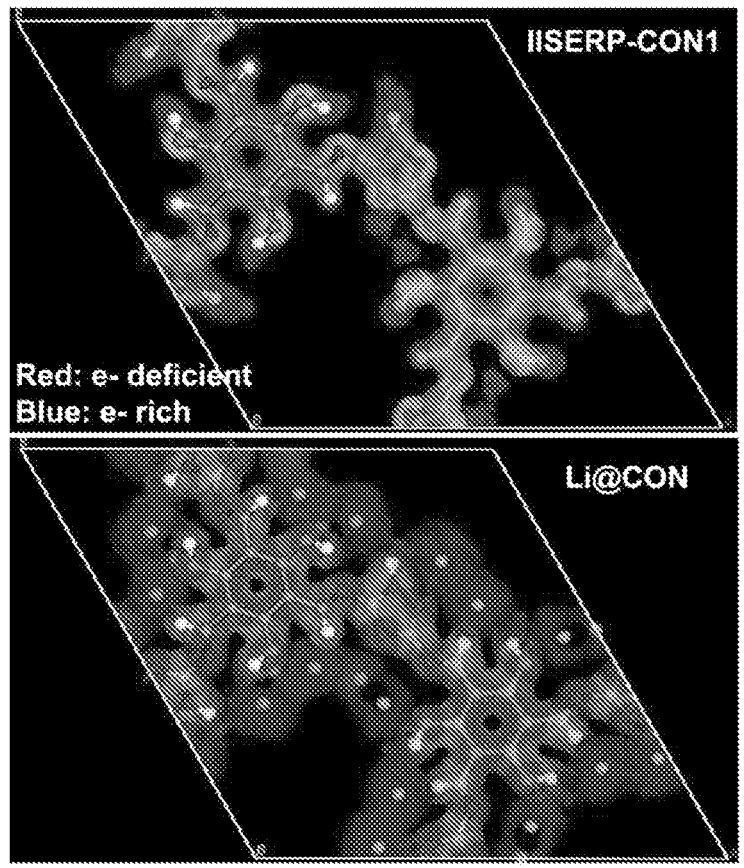

FIG. 22. A comparative electron density plot showing the difference in the e-density distribution and the electrostatic potentials between the pristine IISERP-CON1 and the lithium adsorbed phase of the CON. The CON gets highly activated under the electrostatic influence of the lithium ions.

Figure 23A:
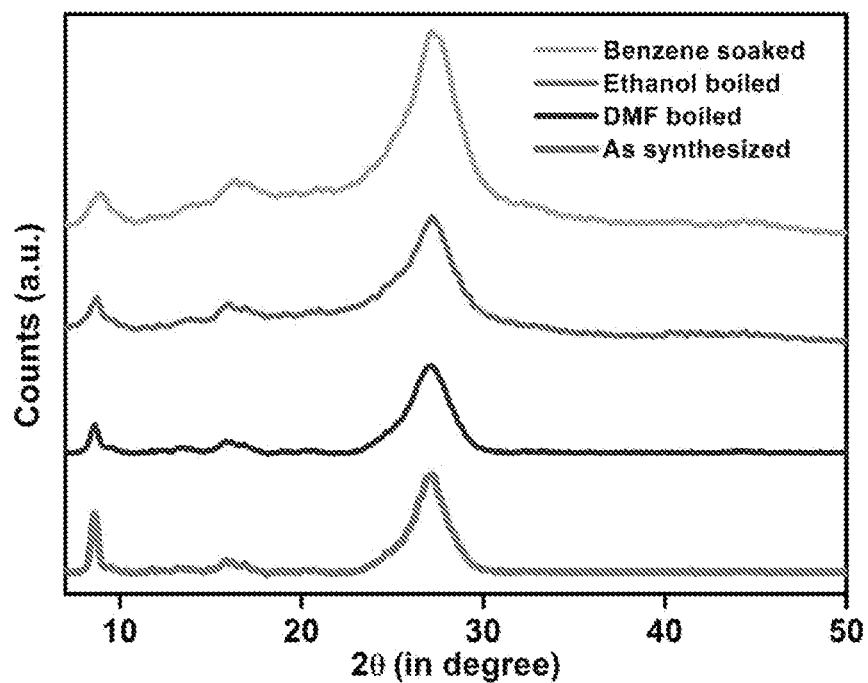
Figure 23B:
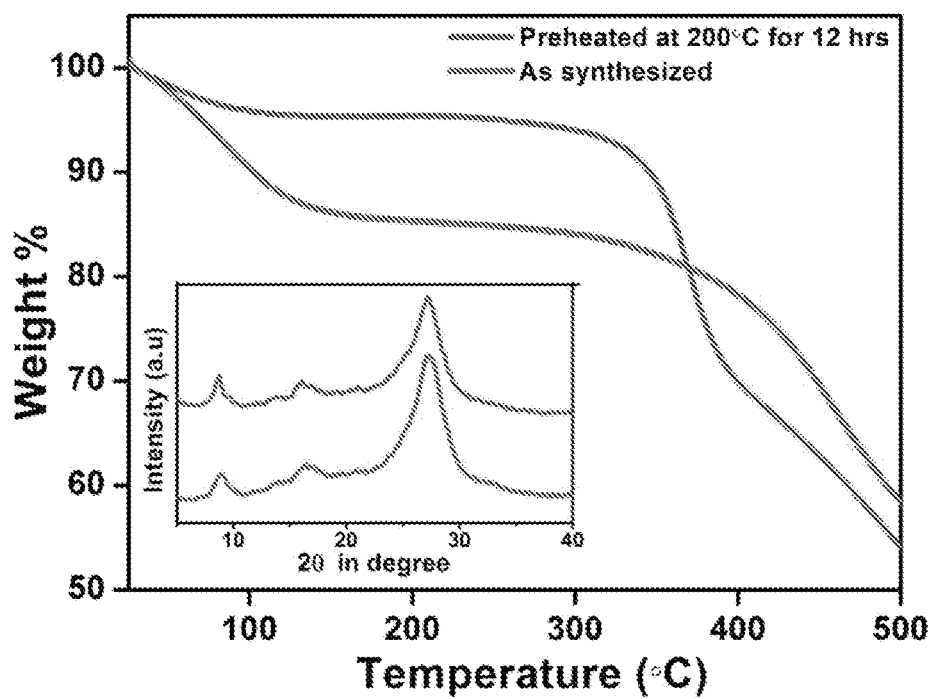

FIG. 23A shows a PXRD pattern of IISERP-CON1 after boiling in DMF and ethanol, soaking in Benzene for 24 hrs. No significant alterations in the PXRD patterns are noted which confirms the stability and structural integrity of the CON. FIG. 23B shows TGA profiles of as made and preheated IISERP-CON1, respectively. TGA were done under N2 atmosphere at 5K/min. Inset: Comparison of PXRD pattern between as made and preheated condition.

Figure 24:
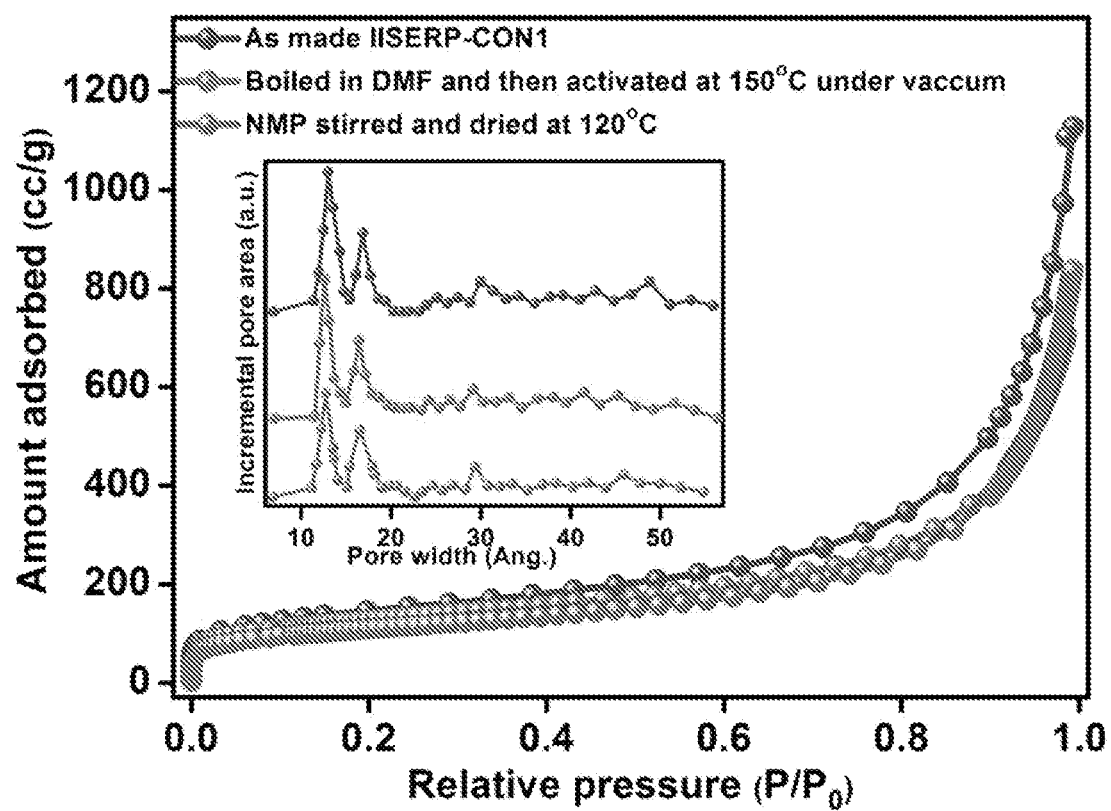

FIG. 24: Comparison of the porosity between the as-synthesized IISERP-CON1, DMF boiled IISERP-CON1 and N-methylpyrollidone (NMP) soaked and dried at 120° C. for 12 hrs under vacuum ($10^{-4}$ Torr) showing no change in the pore-structure. Pore size distribution (inset) shows no significant change of pore dimension in all cases. Note: NMP was used as solvent in the electrode making.

Figure 25:
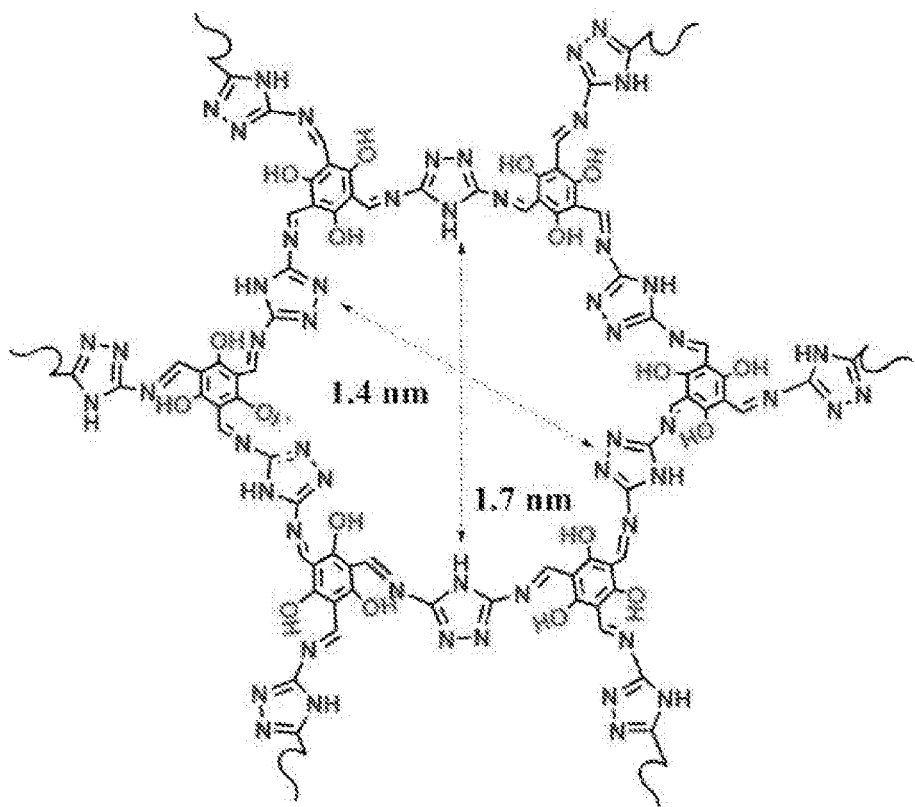

FIG. 25 shows the structure of covalent organic nanosheets (CON) according to the present invention.

ABBREVIATION

IISERP-CON1: CON based on 5-membered 2,4-diamino-triazole (3,5-diaminotriazole) and triformyl phloroglucinol, prepared in accordance with the invention

DETAILED DESCRIPTION OF THE INVENTION

The invention will now be described in detail in connection with certain preferred and optional embodiments, so that various aspects thereof may be more fully understood and appreciated.

The present invention provides Self-exfoliated covalent organic framework (COFs) derived nanosheets (CONs) comprising plurality of 3,5-diaminotriazole units and plurality of triformyl phloroglucinol units, in extended layered covalent framework wherein, the triazole based diamine units are mildly bonded to the triformyl phloroglucinol units. The novel COFs according to the invention even during synthesis has grown into self-exfoliated covalent organic nanosheets (CONs) with exceptional stability and high porosity that can be attributed to its keto-enol tautomerism stabilized framework.

Figure 6A:
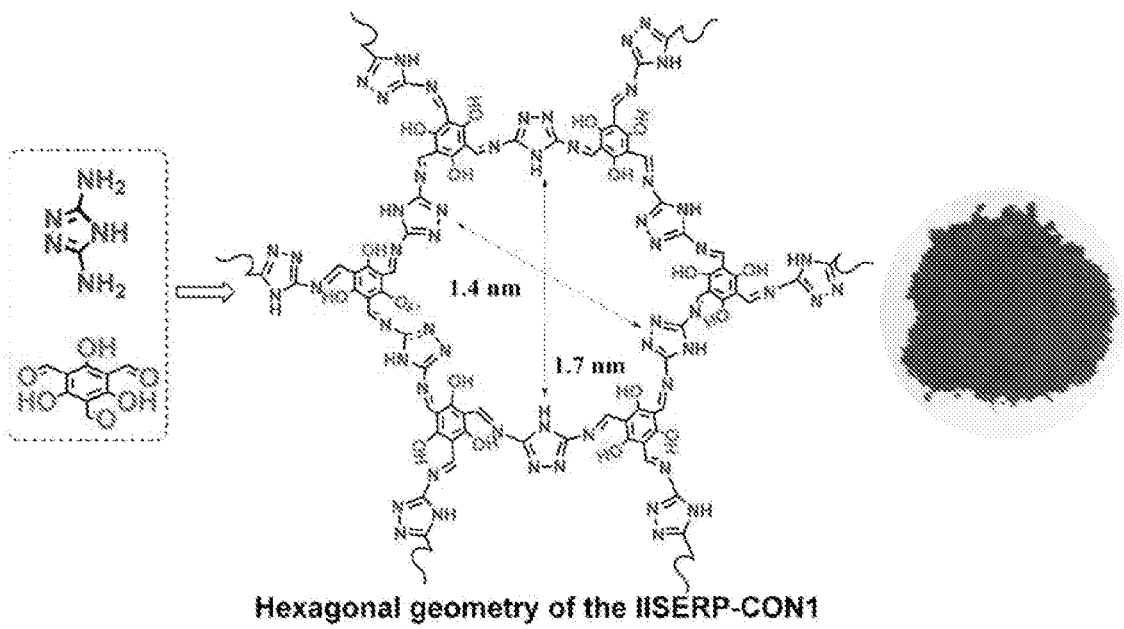
FIG. 6A shows a schematic representation of the reaction procedure used for the synthesis of the highly functionalised IISERP-CON1.
Figure 6B:
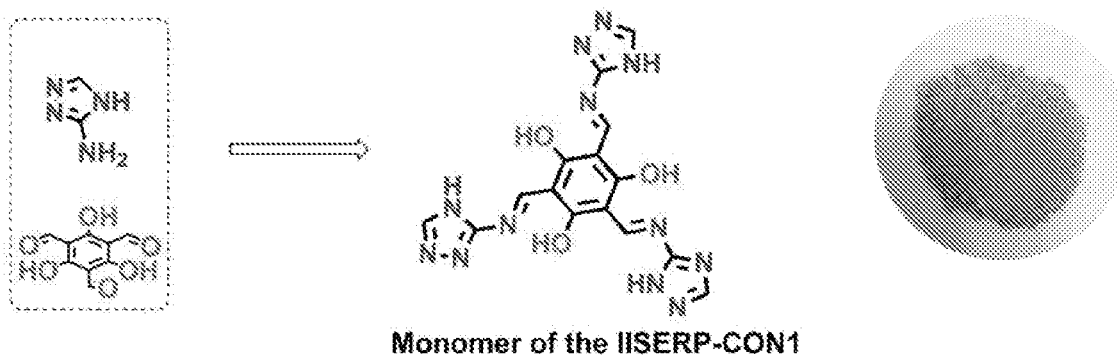
FIG. 6B shows a schematic representation of the reaction procedure used for the synthesis of the monomer used to make the highly functionalised IISERP-CON1. Inset shows the texture and colour of the products.

In another embodiment, the IISERP-CON1 is prepared by a process which comprises;
  a) reacting triformyl phloroglucinol and 3,5-diaminotriazole in dioxane in presence of dimethylacetamide and mesitylene under stirring;
  b) adding 6M aqueous acetic acid followed by flash frozen the reaction mass in a liquid nitrogen bath; and
  c) heating the mixture at 120° C. for sufficient period of time followed by cooling to obtain covalent organic nanosheets (FIG. 6).

Accordingly, the present invention provides a novel CONs (COF-derived nanosheets) based on 5-membered 3,5-diaminotriazole and triformyl phloroglucinol with exceptional stability and high porosity. The presence of triazole rings bring sufficient flexibility to the framework and being short ($\angle NCN=120°$ linker), they assemble the different functionalities in close proximity. The covalent organic nanosheets (CON) according to the present invention can be represented by the structure of FIG. 25.

The covalent organic nanosheets according to the present invention exhibits a BET surface area of about 507 m2/g; a pore volume of about 0.37 cc/g; N2 uptake 77K (~220 cc/g); thermal stability over 300° C. without significant weight loss. According to another embodiment, the invention provides a device which comprises the covalent organic nanosheets of the present invention. The device as referred herein above is selected from the group consisting of solar cells, batteries, capacitors etc. The use of the covalent organic nanosheets (CONs) of the present invention is demonstrated in the present invention for example, in Lithium-ion batteries (LIB).

Some of the key features of this CONs derived LIB include its high specific capacity ~720 mAh/g at 100 mA/g, which is among the highest reported capacities for self-standing non-graphenic organic materials. Importantly, the cell retains this high specific capacity even after 100 cycles. They display only a little drop (~150 mAh/g) in specific capacity even at current densities as high as 1 A/g and it retains a specific capacity as high as 460 mAh/g even at 2 A/g. Simulations using Density functional theory (DFT), coupled with analytical studies, help to identify the lowest energy configuration of the Li@CON, which has a structure with optimal Li-framework interactions. Also, the electronic driving force for the insertion-deinsertion of Li species is established from band structure and electron-density/potential maps.

Figure 1A:
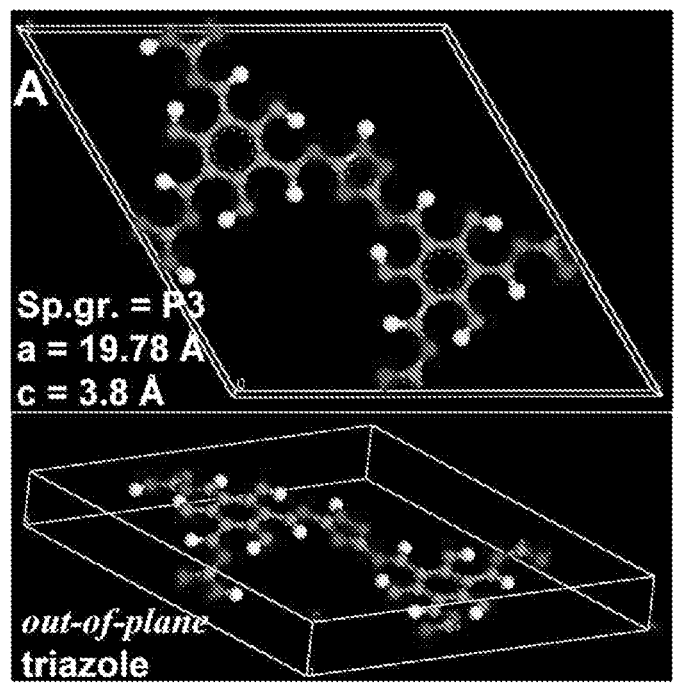
FIG. 1A shows a unit cell of IISERP-CON1 showing the phloroglucinol units placed in different planes cross-linked by 5-membered ring of the triazole unit.
Figure 1B:
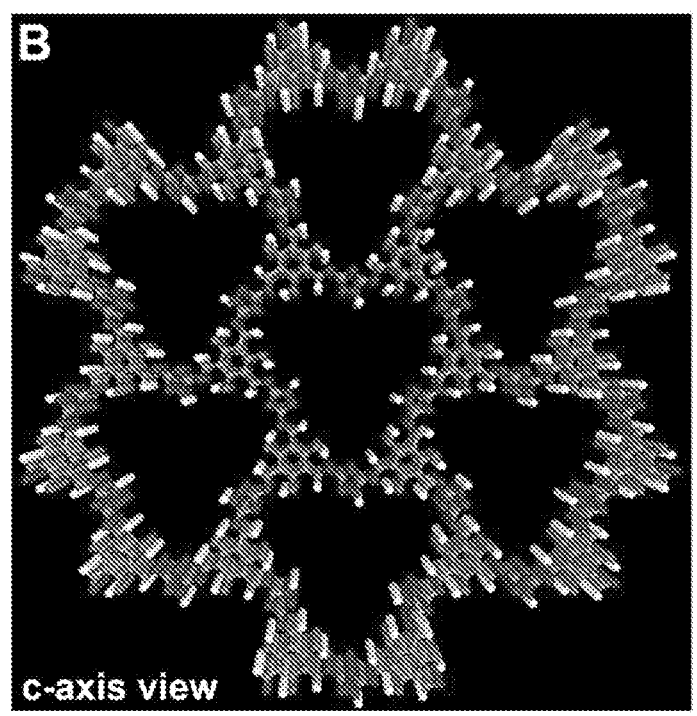
FIG. 1B shows a framework structure showing the triangular pores along C-axis with dimensions 13 (shortest non-covalent atom-to-atom distance) and 16 Å (longest atom-to-atom).
Figure 1C:
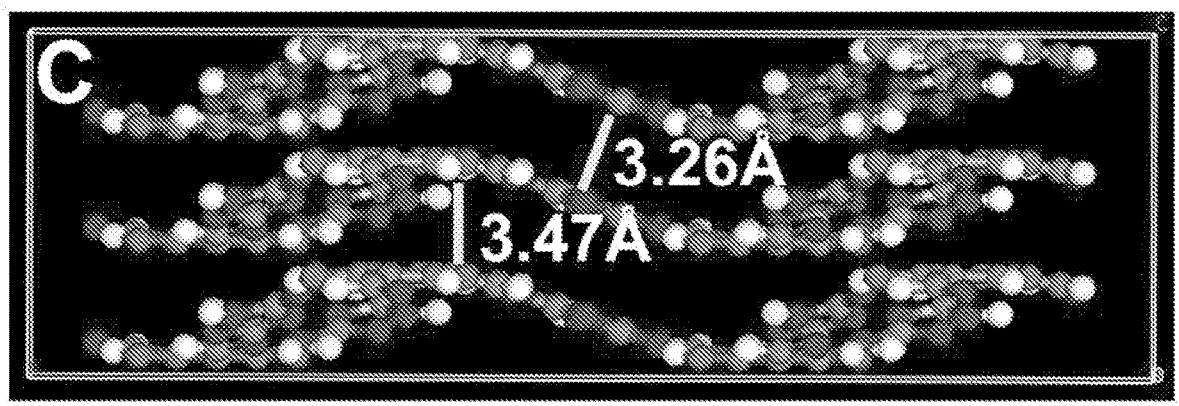
FIG. 1C shows buckled layers of IISERP-CON1.
Figure 1D:
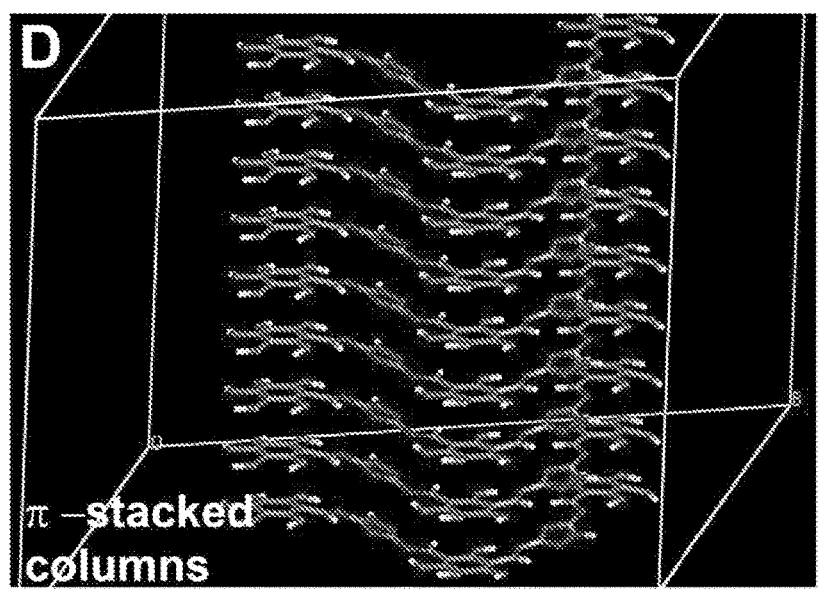
FIG. 1D shows a uniform columnar pi-stack of phloroglucinol units and the triazole units.
Figure 1E:
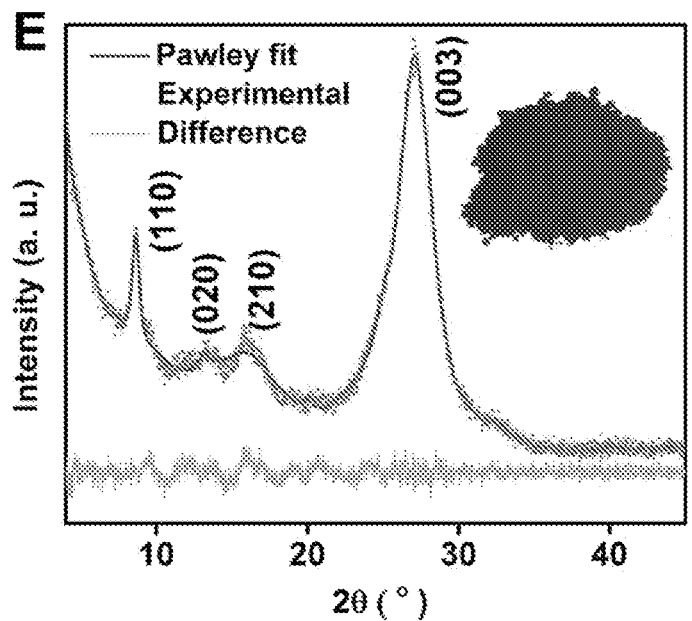
FIG. 1E shows a Pawley fit to the experimental PXRD.
Figure 1:
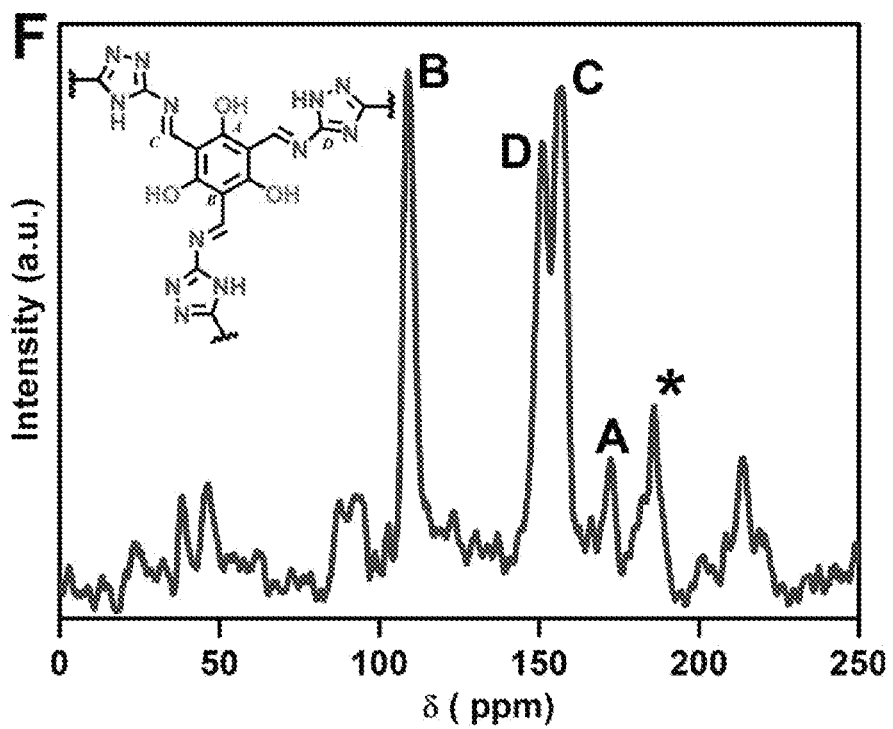
FIG. 1F shows atom assigned 13C-SSNMR.
FIG. 1G shows nitrogen adsorption isotherm at 77K. Inset shows the pore size distribution from a DFT fit.

In an embodiment, the invention provides the structural evaluation of the covalent organic framework of the present invention, the first extended organic framework incorporating 5-membered heterocyclic rings in its construction (FIG. 1). From a Pawley refinement of the indexed powder pattern, the inventors have modeled the most probable structure in P-6 space group. This model has a 2D structure wherein planar hexagonal layers are held together in an eclipsed arrangement by mutually pi-stacking Phloroglucinol and Triazole rings. To obtain the lowest energy configuration, the geometry of the 2D hexagonal model is optimized using periodic tight binding Density Functional Theory method. A fully cell and motion group relaxed optimization resulted in a solution in P3 space group, which had ~8 kcal/mol lower relative energy. In this lowest energy structure, the layer flexes around the 5-membered pivot giving rise to a wavy 2-D stack (FIGS. 1C and 1D). The triazole rings buckle out-of-plane and cross-links with the phloroglucinol in the ab-plane. Such out-of-plane flexibility from the 120° linking triazole units are reminiscent of the modes found in the imidazole rings present in the ZIF structures. It is observed that the phloroglucinols from the adjacent layers pi-stacked at distance of 3.47 A, while the triazole units stacked at a distance of 3.26 A.

During the growth, these COF layers self-exfoliate, hence there are not sufficient number of layers in the particulates to give rise to strong intensity peaks in the X-ray diffraction, this explains the lack of intensity for the (100) reflection (FIG. 1E). This agrees well with the observations made by Banerjee and co-workers. Other experimental evidences confirm that this covalent organic nanosheet (CON) structure as the most probable, come from the porosity measurements (FIG. 1G), the Field Emission-Scanning Electron Microscopy (FESEM), Field Emission-Transmission Electron Microscopy (FETEM) and Atomic Force Microscopy (AFM) studies (FIG. 2). The material shows excellent N2 uptake 77K (~220 cc/g in the P/P0 range of 0-0.8 and a characteristic pore condensation at higher P/P0 region). Such high uptakes confirm its behaviour resembling COF-derived nanosheets and discount any chance of these being simple discrete cages, which usually show significantly lower porosities. (The samples were subjected to rigorous soxhlet extraction to ensure no unreacted materials or soluble oligomers/cages are left behind).

Figure 1G:
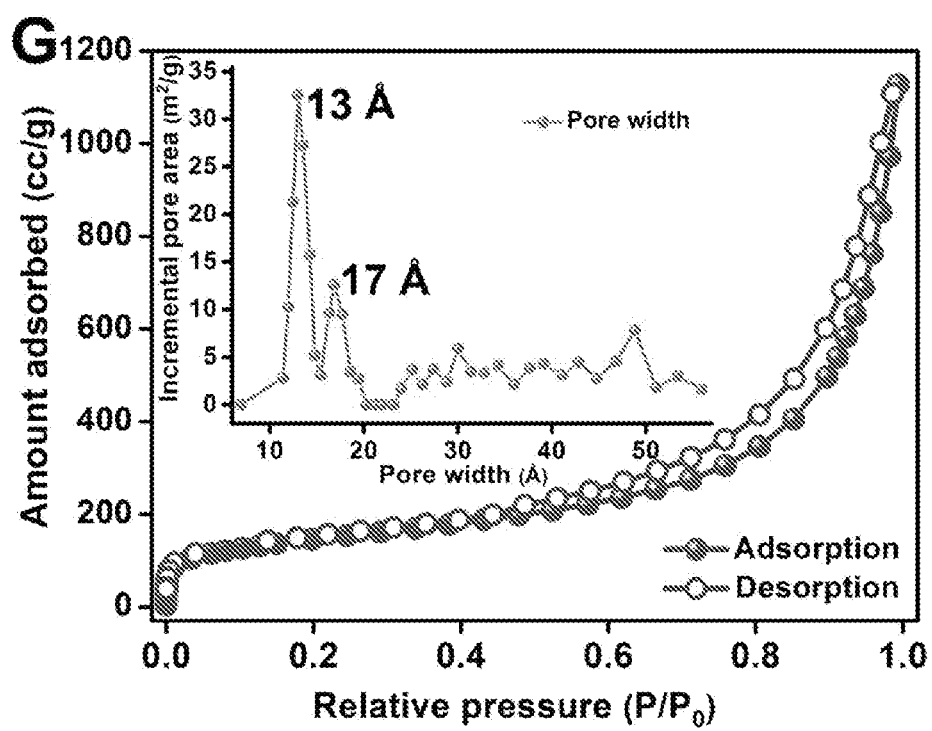
Figure 2A:
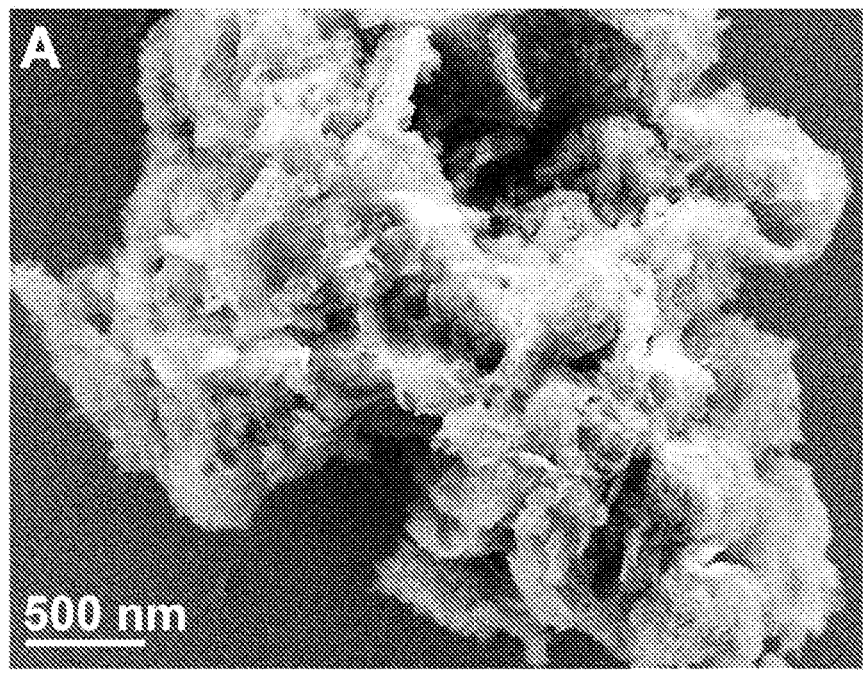
FIG. 2A shows a FE-SEM image of IISERP-CON1, the inset is a zoom-in showing the fluffy flaky morphology.
Figure 2B:
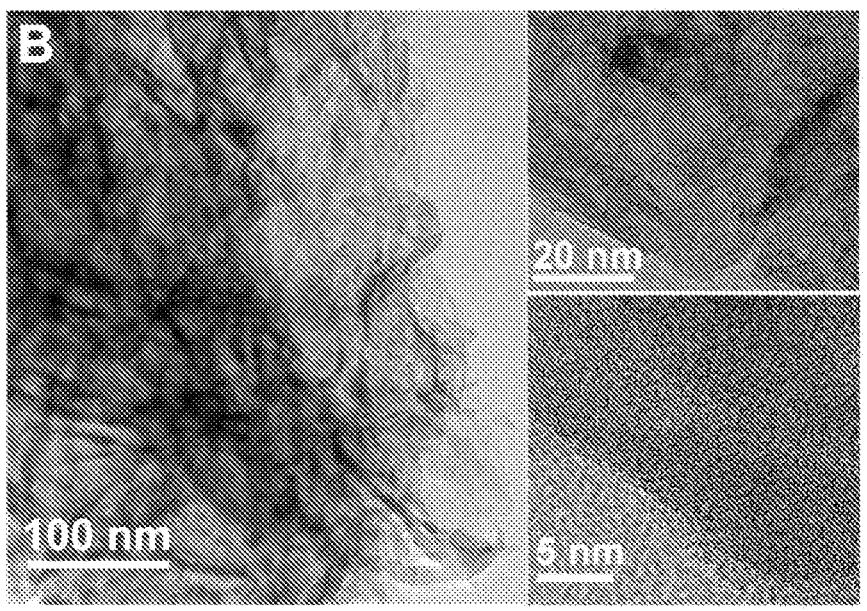
FIG. 2B shows a HRTEM image showing typical thin layers of the nanosheets with inundated or wrinkled surface.
Figure 2C:
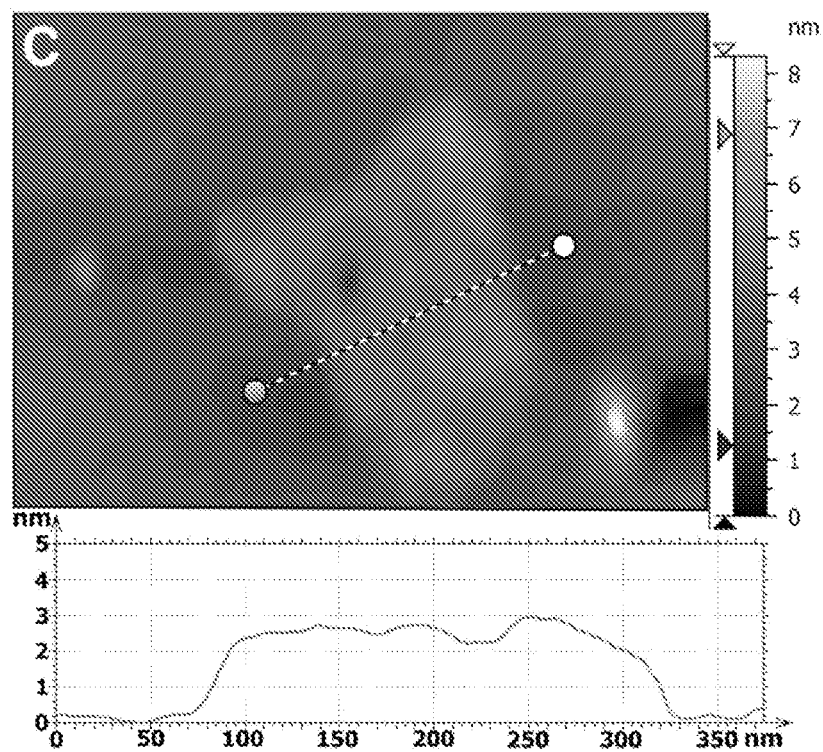
FIG. 2C shows HRTEM images showing the small micropores on the surface of the nanosheets.
Figure 2D:
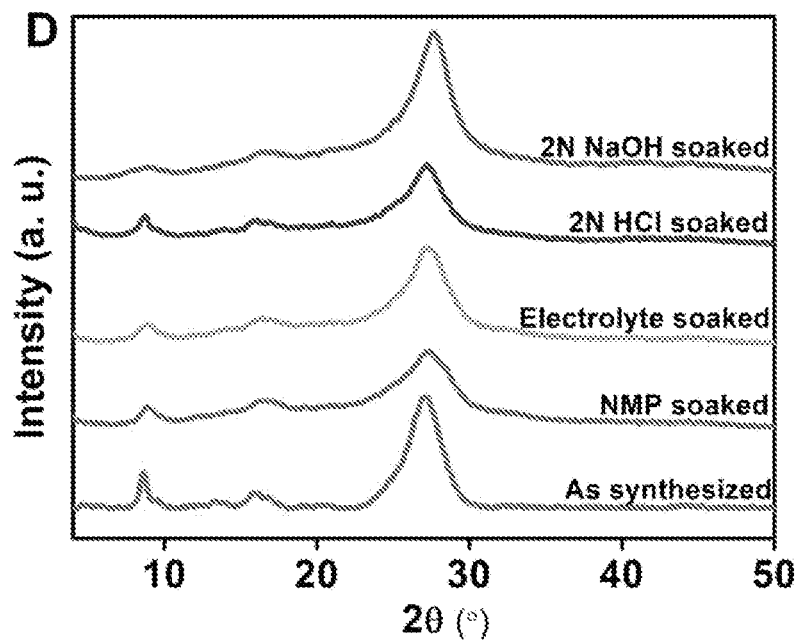
FIG. 2D shows the image and 3D construct from the AFM showing the nanometer thickness of these drop-casted samples. The height profile plot quantifies it to be in the range of <3 nm.
Figure 7A:
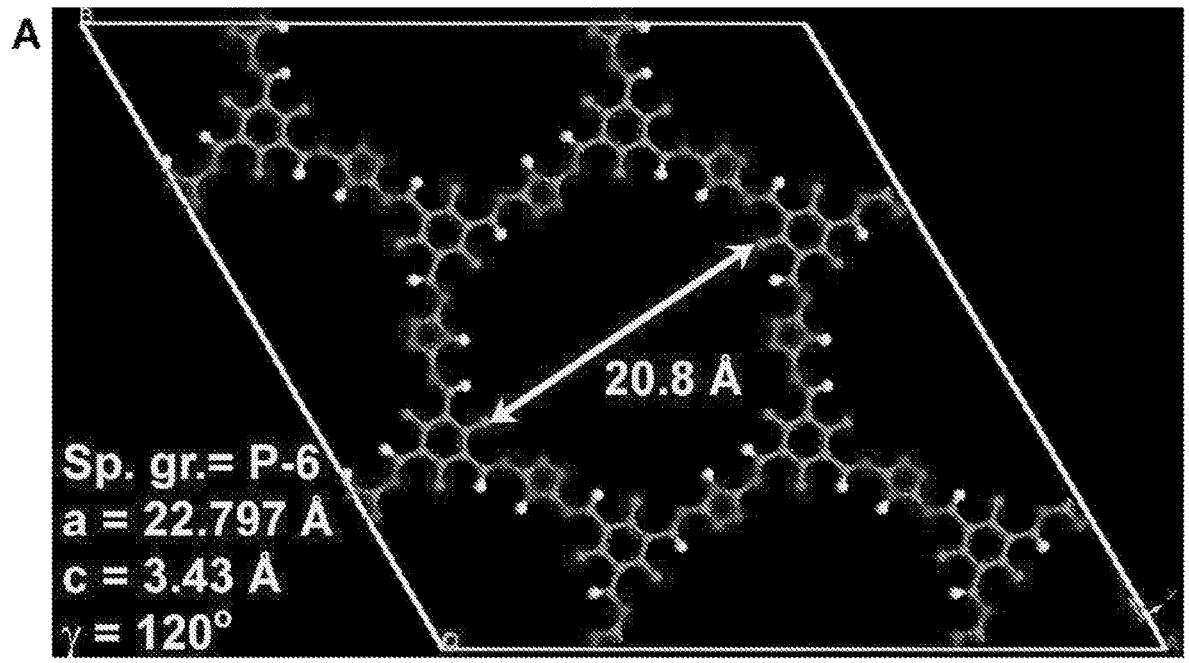
FIG. 7A shows a model structure of the IISERP-CON1 obtained using Pawley refinement with a perfectly planar structure.
Figure 7B:
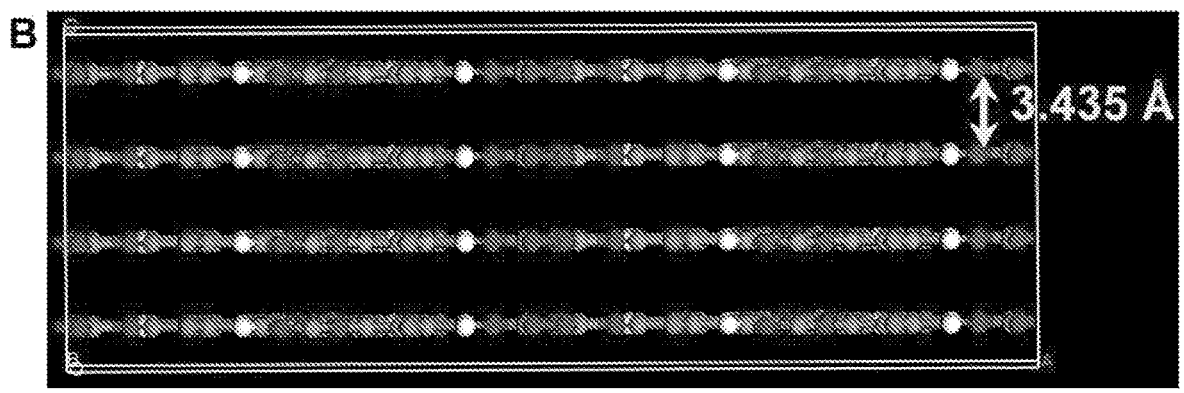
FIG. 7B shows stacked layers with interlayer separation of 3.796 A. This has an energy 8 kcal higher than the actual structure proposed for the IISERP-CON1 with buckled layers.
Figure 8A:
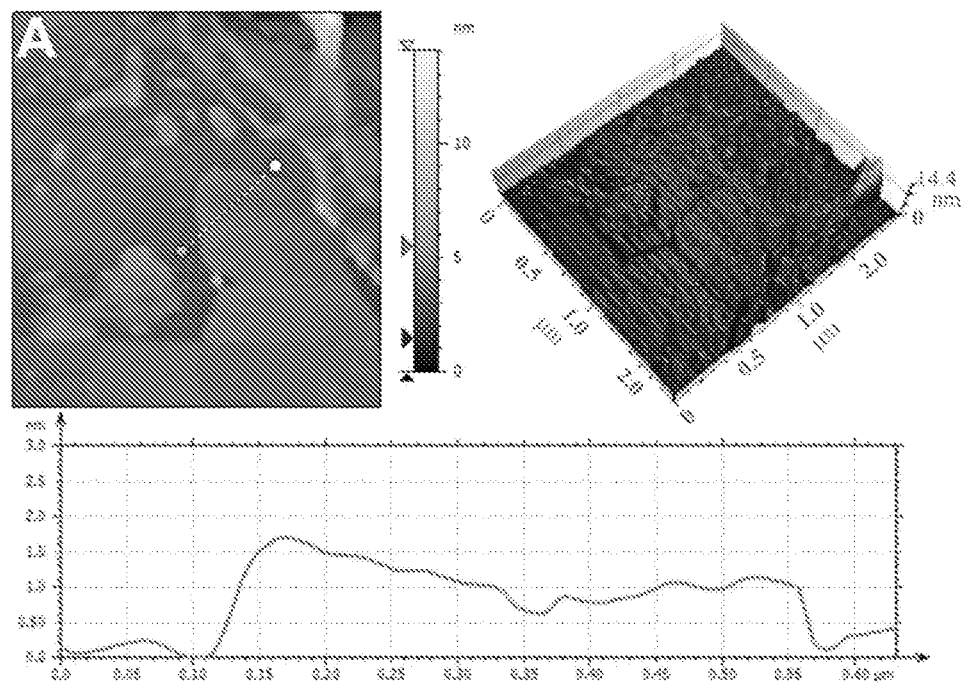
FIGS. 8A, 8B, 8C, and 8D: AFM images of the CON, its height profile and 3D view from different regions of drop-casted sample prepared in THF. It shows an average thickness in the range of ~1.5 to 2 nm suggesting the sample forming as uniform self-exfoliated nanosheets.
Figure 8B:
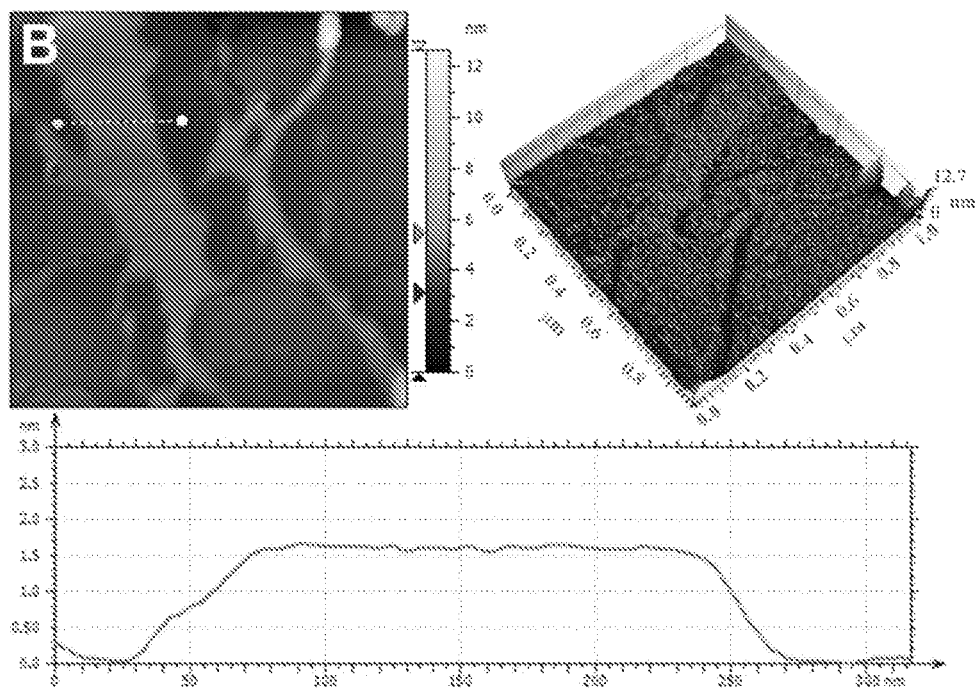
Figure 8C:
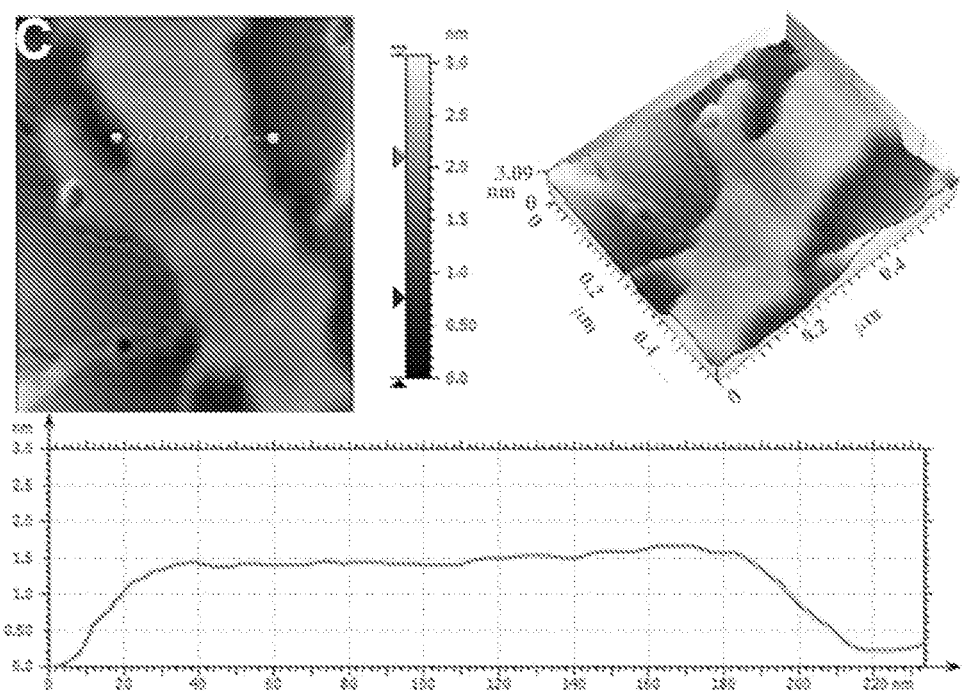
Figure 8D:
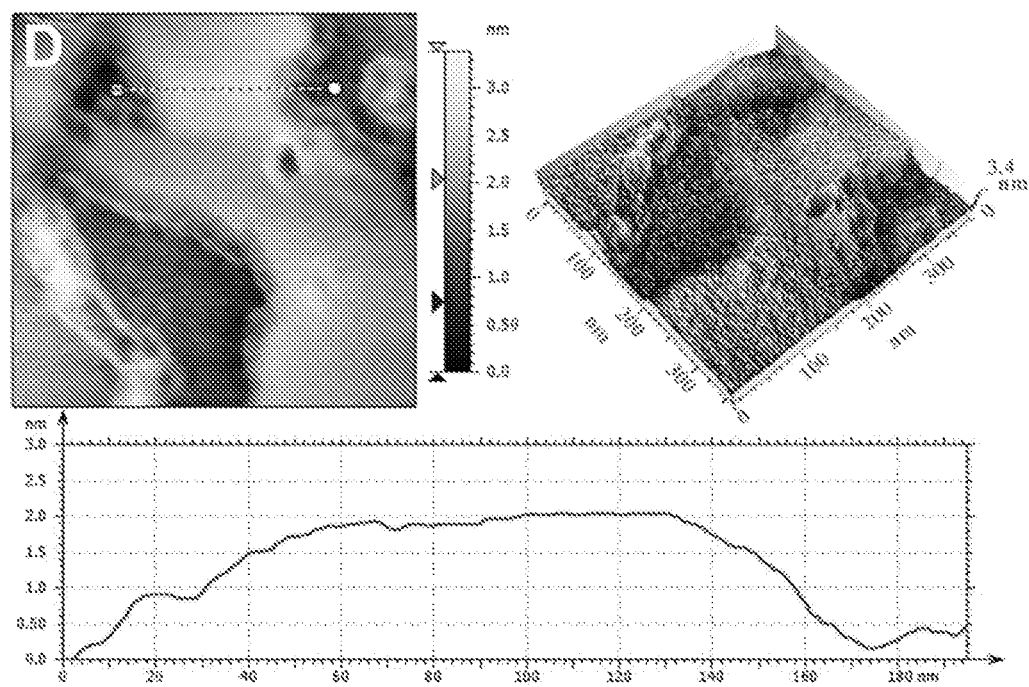

Further, the pore size distribution estimated from the 77K N2 isotherms using a DFT fit shows majority of the micropores are concentrated around 13 and 16 Å, and the presence of hierarchy of pore sizes in the mesoporous regime (FIG. 1G). IISERP-CON1 exhibits a BET surface area of about 507 m2/g and DFT fit yielded a pore volume of about 0.37 cc/g. This is characteristic of such nanosheets. If the material had adopted the perfectly planar hexagonal sheet structure there should have been uniform 1-D channels of 21 A pores (FIG. 7), which was not the case. Also, the material is practically insoluble in any of the common organic solvents even under boiling conditions, which excludes it from being a mere organic cage or oligomer. The IISERP-CON1 shows good thermal stability over 300° C. without significant weight loss; and chemical stability toward different solvents, electrolytes, and acidic media (FIGS. 23 and 24). Under the Field Emission Scanning Electron Microscopy (FESEM) also these nanosheets show fluffy cotton-like morphology (FIG. 2A) reminiscent of commercial high surface area graphenes, rather than the plate-like morphology observed for highly ordered hexagonal COFs. Furthermore, the FE-TEM images recorded on the material showed typical exfoliated-COF like morphology-thin layers rolled up giving a more inundated surface resembling graphenes. From a higher resolution FE-TEM image (5 nm), the fine porous surface of the nanosheets could be observed (FIG. 2B).

Furthermore, the High Resolution Transmission Electron Microscopy (HRTEM) images recorded on the material showed typical COF-derived or exfoliated-COF like morphology, thin layers rolled up giving a more inundated surface. From a higher resolution HRTEM image (5 nm), the fine porous surface of the nanosheets could be observed. Another strong evidence for the presence of few layers thick nanosheets came from the Atomic-force microscopy (AFM). The height profile from the AFM images of a drop casted sample showed thickness of ~2-5 nm, which is in consistent with previous observations. In contrast, typically well-grown COFs tend to contain more number of stacked layers with thicknesses of few hundred nanometers. Also, the AFM images from different samples and different regions of the sample showed that such few nm thick layers were uniformly distributed across the samples (FIG. 8).

In another embodiment, considering the morphological and more importantly the structural resemblance of these covalent organic nanosheets to exfoliated carbonaceous structures and the presence of multiple organic functionalities (—OH, —C=N—, triazole rings and aromatic carbons) that can interact with inorganic cations; a further investigation was carried into the potential of this material as an electrode material for a device such as Lithium-ion batteries.

Figure 3A:
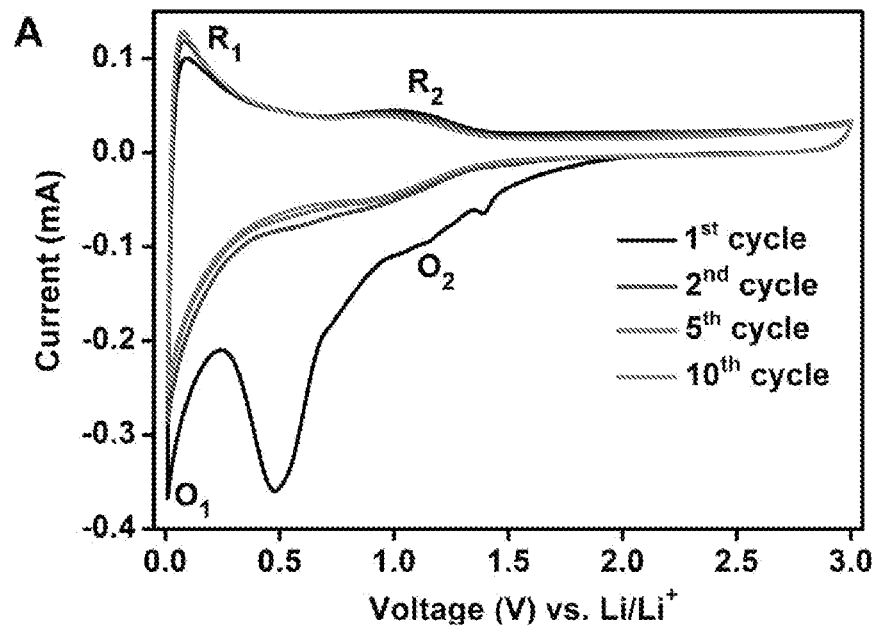
FIG. 3A shows a CV curve showing the presence of two redox peaks due to the intercalation (0.02V) and binding (~1V) of Lithium into the CON.
Figure 9:
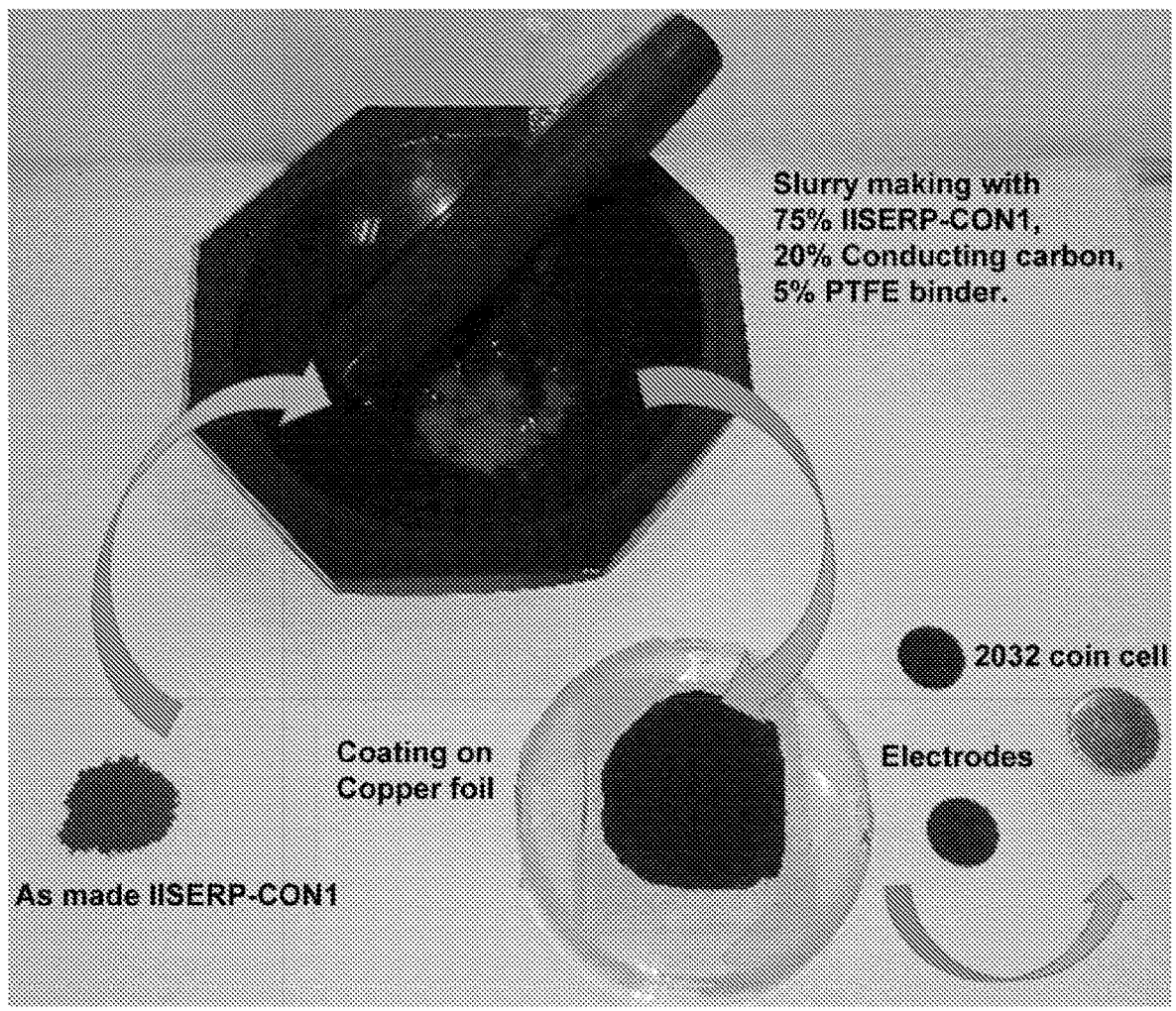
FIG. 9: Schematic representation of coin cell preparation for electrochemical measurements.

Accordingly, in an exemplary embodiment, a coin cell battery assembly was fabricated in an Argon-filled glove box using a slurry made by mixing CON, Conducting Carbon and PTFE binder in N-methylpyrrollidine in a ratio of 70:25:5 (FIG. 9). The slurry coated onto a copper foil (current collector) was used as the anode, which was separated by the electrolyte, a paper wetted with a 1M LiPF6 solution using a (1:1) dimethyl and ethyl carbonate mixture as the wetting solvent. Neat lithium metal was used as the counter and the reference electrode. To investigate the lithium insertion-deinsertion characteristics of the MEA (Membrane electrode assembly), a coin cell (2032) assembly was engaged by connecting to a charge-discharge unit. A cyclic voltammogram (CV) was measured using a 0.2 V/Sec sweep-rate in the potential window of 0.01 to 3 Volts (FIG. 3A). In its 1st cycle, the CV shows a prominent peak at 0.48V corresponding to the formation of solid electrolyte interphase (SEI) layer and the corresponding current is –0.36 milli amperes (mA). From the 2nd cycle onwards the peak due to the SEI layer formation diminishes leaving a stable CV. The sharp peak at very low potential (~0.02V) suggests intercalation of Li into the nano-sheets with little effort. The second significant peak at 1.0 V appears as a broad feature. Importantly, this peak arising from chemical interactions is notably weak compared to what is reported for other COFs and organic material which form true chemical bonds with Li.

Figure 10:
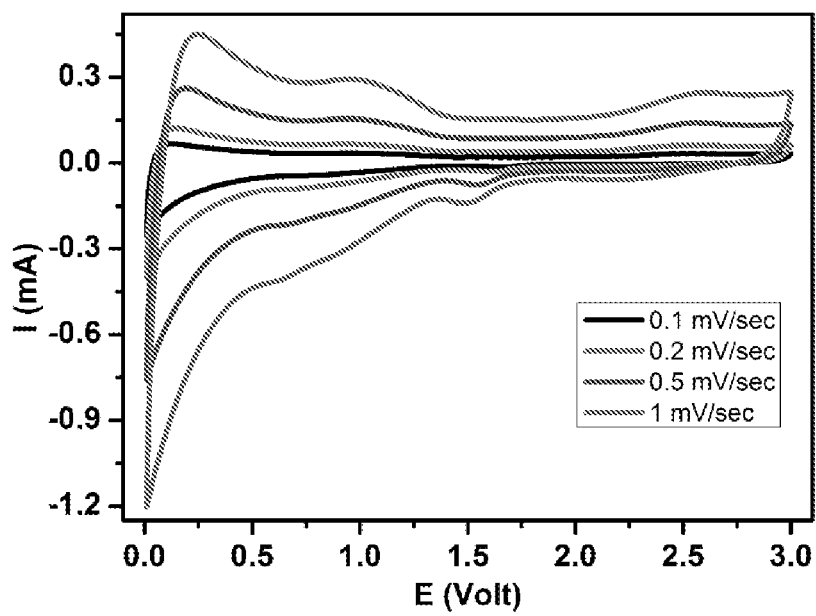
FIG. 10: Cyclic voltammogram plot of IISERP-CON1 loaded coin cell in different scan rates, which was performed after completion of SEI layer formation. Increment of current density with the increment of scan rate indicates capacitive type behaviour. The peaks at 1.5 V (irreversible) and 2.5 V (reversible) are due to the insertion-deinsertion of Lithium species into the conducting carbon in Li ion storage and due to air oxidation of lithium, respectively.
Figure 11:
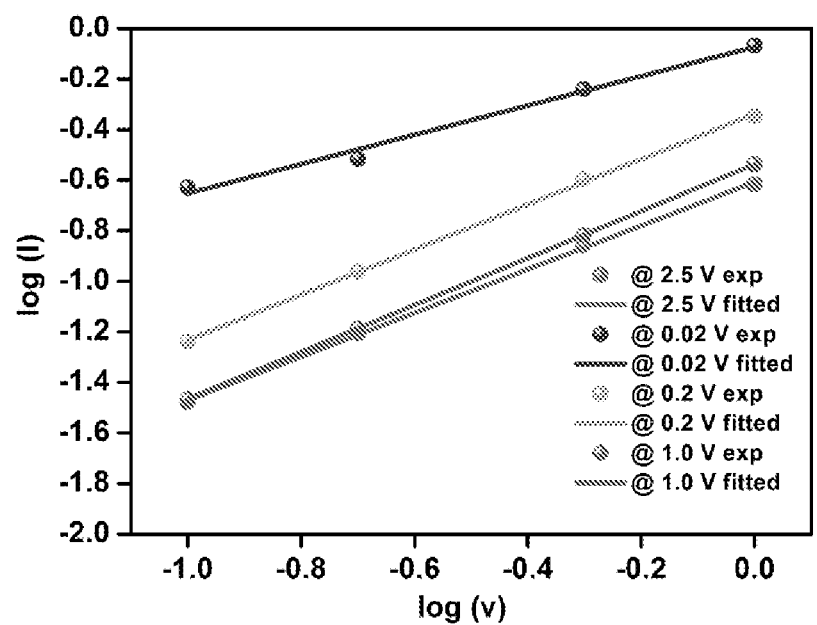
FIG. 11: Logarithm of peak current intensity (anodic) vs logarithm of scan rate at different potentials extracted from CV plots. Note the linear increment of peak current with the increase of current density.

To verify, if there was any capacitive mechanism involved in the COF loading and to confirm that the broad peak at 1.0 V is not merely due to a poor resolution from faster scan rate, a variable scan rate CV was performed (0.1-1 mV s-1; potential window: 0.01-3.0 V) (FIG. 10). A fit to the power law, $i=av^b$ (i=current; v=scan rate), resulted in b=0.5@0.02V which obeys Cottrell's equation suggesting that the Li loading into CON operated mostly via a diffusion-controlled intercalation mechanism (FIG. 11)[21]. While this b value was 0.93 @ 1V and 0.86 @ 2.5V revealing that there is only a little contribution from the surface controlled charge storage behaviour (capacitive). Also, both the anodic and cathodic peak currents vary linearly with the square root of scan rate suggesting that it is mostly mass transfer controlled. Hence realizing high specific capacity depends significantly on the mobility of the Li ions within the bulk of the CON, impedance spectroscopy measurements were utilized. The Warburg coefficient was calculated from the ac impedance measurements and was fitted into the standard ionic diffusion expression. The lithium diffusion coefficient was calculated to be DLi+ of 5.48×10-11 cm2 s-1, which is quite comparable to those reported for Li diffusion in other graphitic as well as 2D inorganic materials.

Figure 3B:
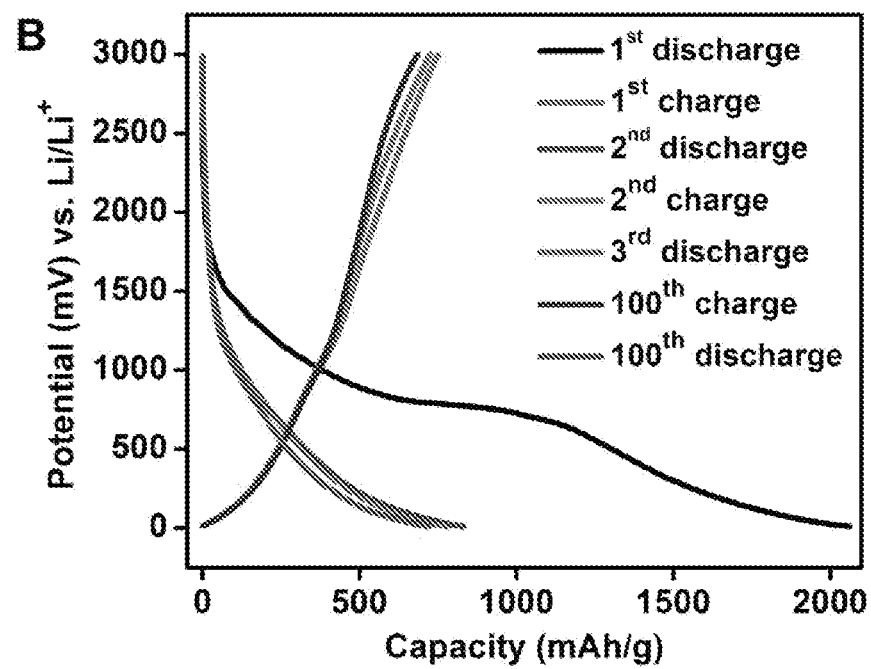
FIG. 3B shows a Charge-discharge cycling measurements showing the high cyclability. The thermal (blue) and compression (red) components of the PE are shown. For comparison, values calculated by Huck et al. are shown as black lines.
Figure 3C:
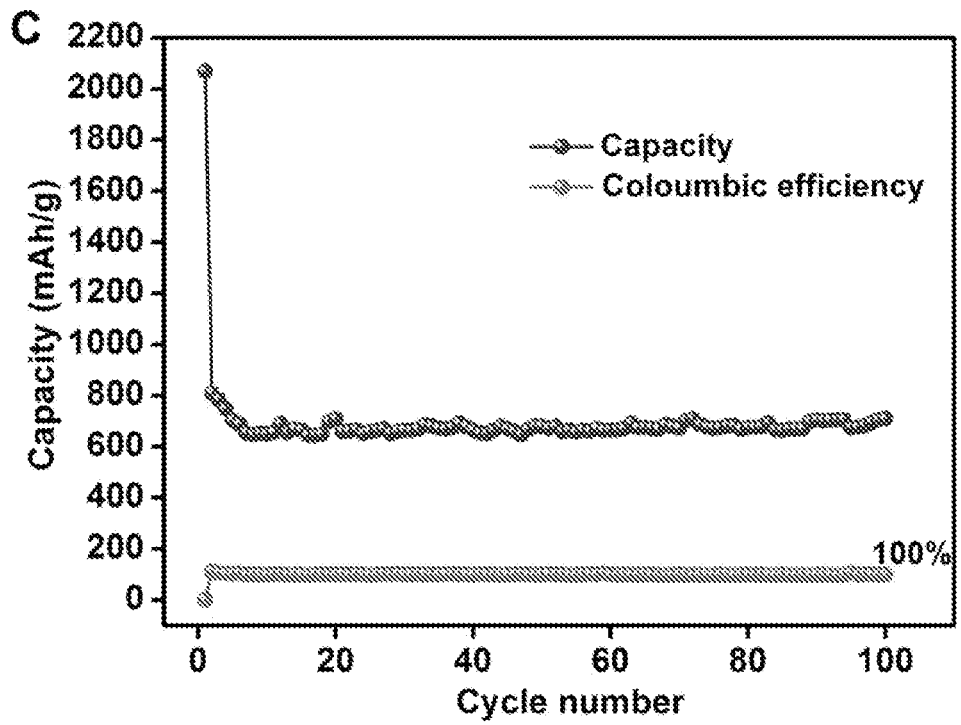
FIGS. 3C and 3D show plots of charging capacity.
Figure 3D:
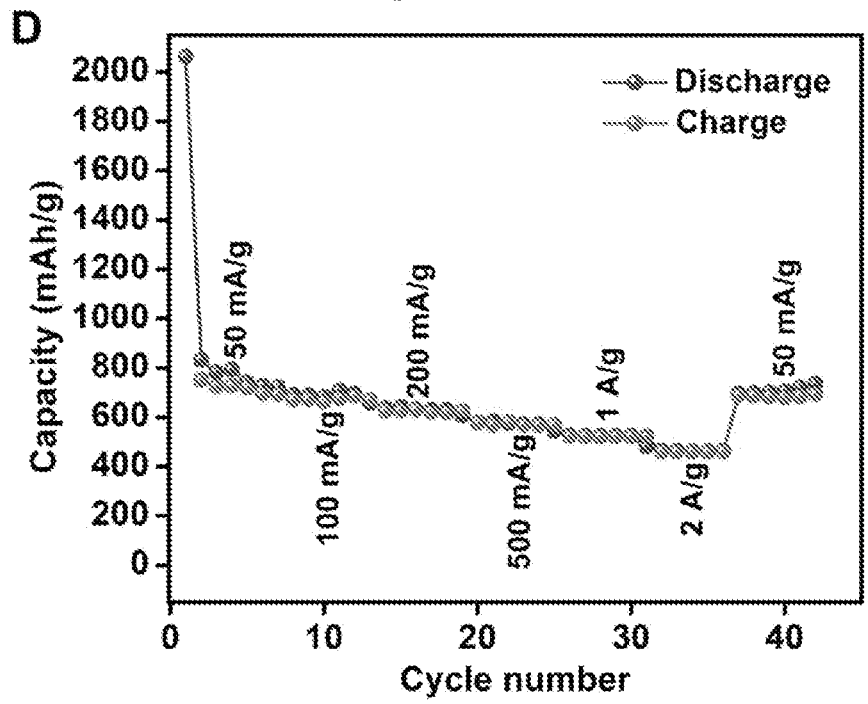
Figure 12A:
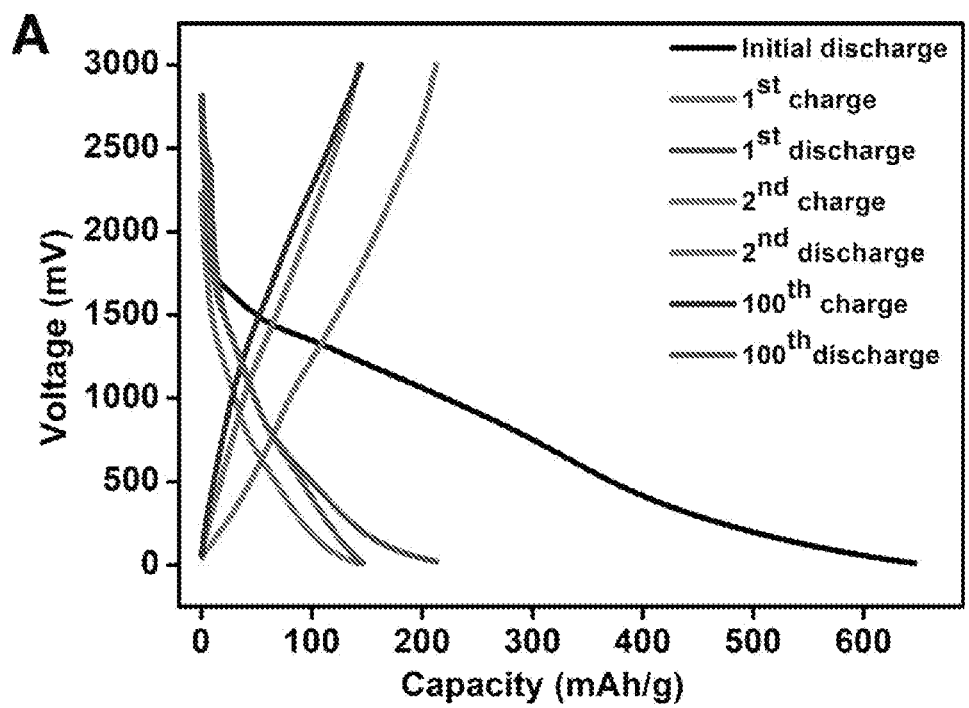
FIG. 12A shows a Galvanostatic charge-discharge curves for the monomer.
Figure 12B:
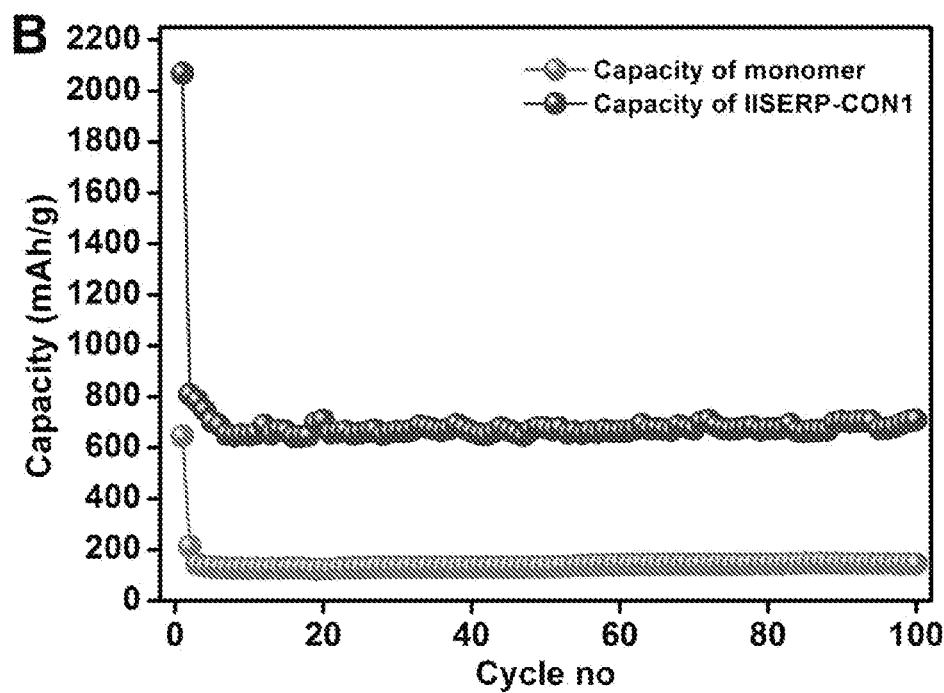
FIG. 12B shows a comparison of the cycle performance at a current density of 100 mA/g for IISERP-CON1 (blue curve) & monomer (green curve).
Figure 13:
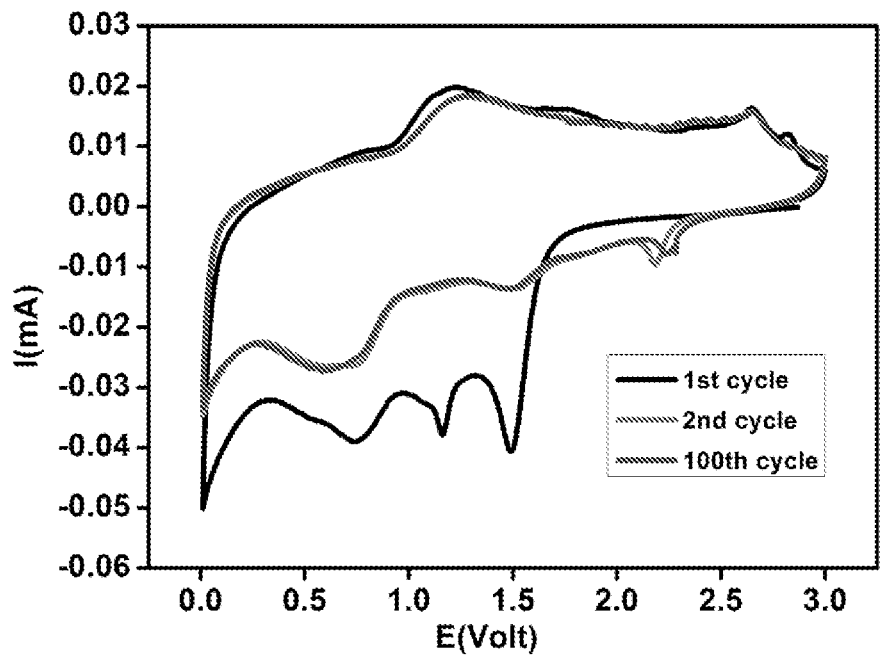
FIG. 13: Cyclic Voltammogram plot of IISERP-CON1 monomer loaded coin cell in $1^{st}$ cycle, $2^{nd}$ cycle and after 100 cycles. There is no significant intercalation peak at low potential like π-π stacked IISER-CON1. But from 0.6 V it gives peak for reversible chemical interactions only.
Figure 14:
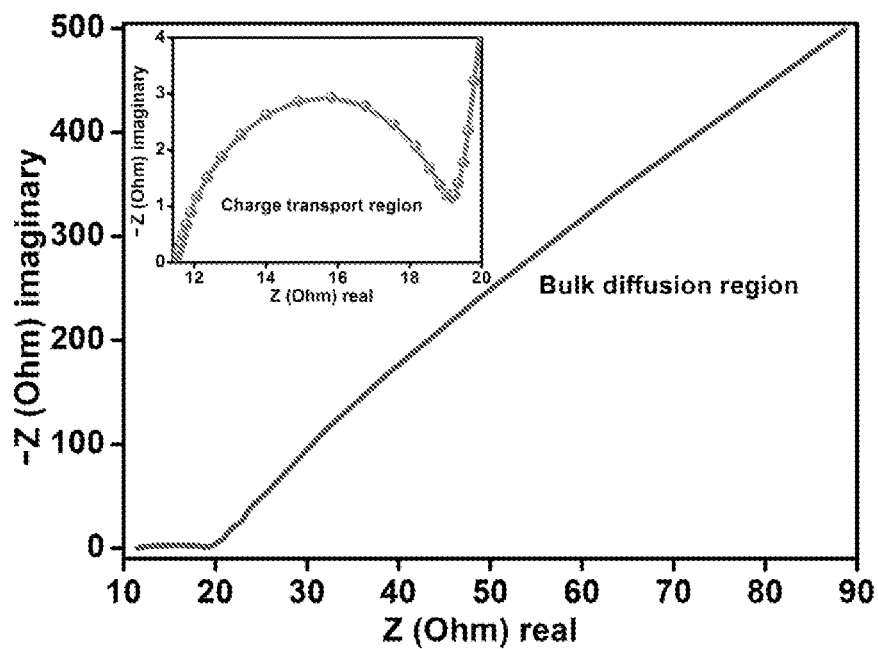
FIG. 14: Nyquist plots of IISER-CON1 electrode after completion of SEI formation in first cycle (blue curve). Inset: a zoom-in showing the intercepts.

Galvanostatic charge-discharge sweeps at a current density of 100 mA/g corroborate well with the I-V features in the CV curves (FIG. 3B). A peak centered at around 0.48 Volt (FIG. 3A) denotes the formation of SEI layer in the first discharge cycle which yields a very high first discharge capacity of 2060 mAh/g (FIG. 3B). In the 2nd cycle, the capacity drops to 835 mAh/g as the SEI layer formation walks away. Following this, over 100 charge-discharge cycles were carried out. The cell maintains high and stable discharge capacity of 720 mAh/g (@ 100 mA/g) during this prolonged cycling which essentially confirms the potential of the novel CON material of the present invention to act as stable lithium ion battery anode. The charging capacity values in the corresponding cycles are reasonably compatible with the discharge capacities leaving a coloumbic efficiency almost of 100% in every cycle (FIG. 3C). This stable current output can be attributed to the inherent chemical and thermal stability of these nanosheets. Furthermore, only a small drop in specific capacity (150 mAh/g) is observed even at current densities as high as 1 A/g (FIG. 3D). In comparison, other nano-structured materials with high specific capacities for LIB show significant drop in capacity with both increasing current density and under prolonged cycling. This has been explained by the formation of some highly energetic redox species which bind irreversibly with the Li during the battery cycling. The absence of any drastic drop in the specific capacity with increasing current density also suggests fast Li diffusion kinetics, which supports the lack of any sharp peaks in the CV graphs. Thus, the few layer thick CON has the ability for ultrafast discharge/charge process. Its exfoliated structure with hierarchical pores most probably favors faster Li diffusion into shortened paths compared to a highly stacked COF, wherein the slower kinetics could increase the contact time with the active sites leading to unwelcome irreversible chemical binding. However, it is essential to have the covalently bound extended framework structure to realize the observed intercalation assisted Li charge-discharge. For example, when the charge-discharge characteristics and the CV on the monomer formed by reacting the trialdehyde involved in the construction of IISERP-CON1 with 3-amino-1,2,4-triazole, was carried out, the capacity observed was only 140 mAh/g (FIG. 12). More importantly, the CV showed that the intercalation peak expected at 0.02 V was missing and the other peaks due to chemical interaction observed for the IISERP-CON1 were seen (FIG. 13). Interestingly, the Li insertion into the monomer is completely reversible with 100% columbic efficiency. This would mean that the triazole units coupled with the phenolic triformyl units and C6 rings seem to form modules capable of providing apt chemical interactions with Li species and this capability is retained in the CON constructed from these modules. Another contribution to the high activity of the Li-ion cell is from the inherent low resistivity of the CON; impedance measurements reveal that the cell carries a series resistance as low as 11.3 Ohm and shows charge transfer resistance 7.5 Ohm (FIG. 14).

Figure 15:
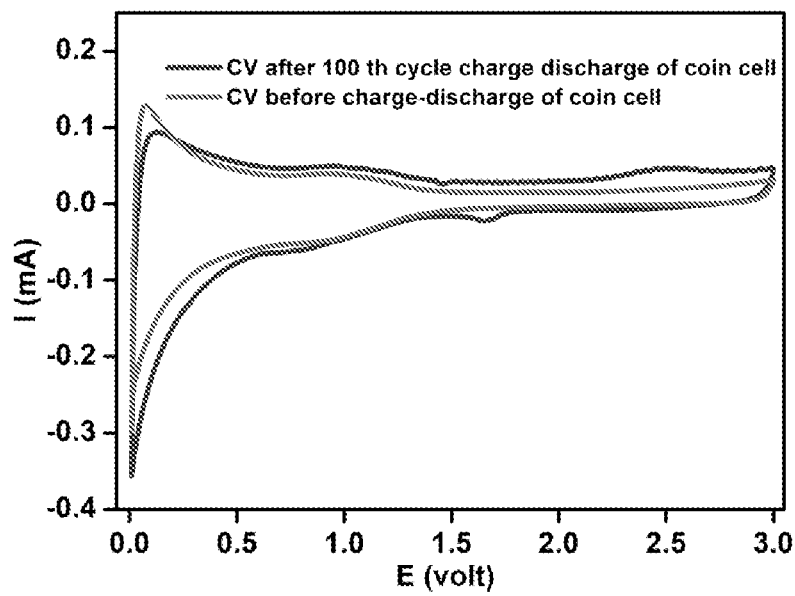
FIG. 15: Cyclic Voltammogram plot of IISERP-CON1 loaded coin cell just after completion of SEI formation in first cycle and after 100 cycles.

The electrochemical cyclic stability of the CON was confirmed from complete retention of its redox activity even after 100 cycles of charge-discharge (FIG. 15). The impedance measurement also confirms the lack of any ohmic loss from the coin-cell assembly over these cycles (see inset of FIG. 16). To further substantiate the integrity of the CON under the applied electrochemical stress, an electrode with neat CON in NMP without using any conducting carbon was made and subjected it to 100 cycles of charge-discharge. From PXRD and IR and FE-SEM measurements (FIG. 17-19), it can be confirmed that the post-cycling material retains crystallinity and chemical structure. In the IR, few new peaks were observed at lower wave numbers, which did not correspond to any covalent Li—COF interactions, hence it can be concluded that these new peaks are due to the weaker interaction of the intercalated Li with the framework.

Figure 4A:
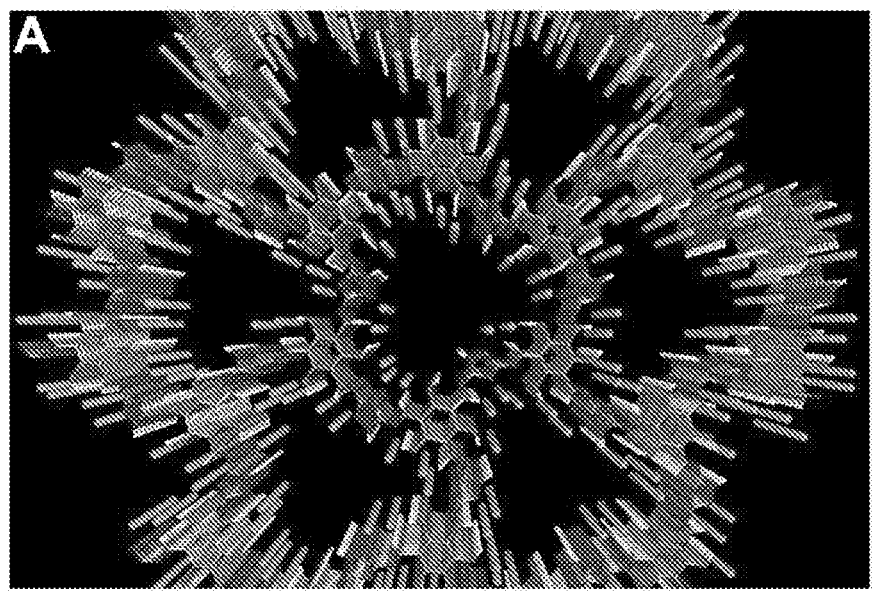
FIG. 4A shows a perspective view of the 3D structure of the lithiated CON obtained from simulations.
Figure 4B:
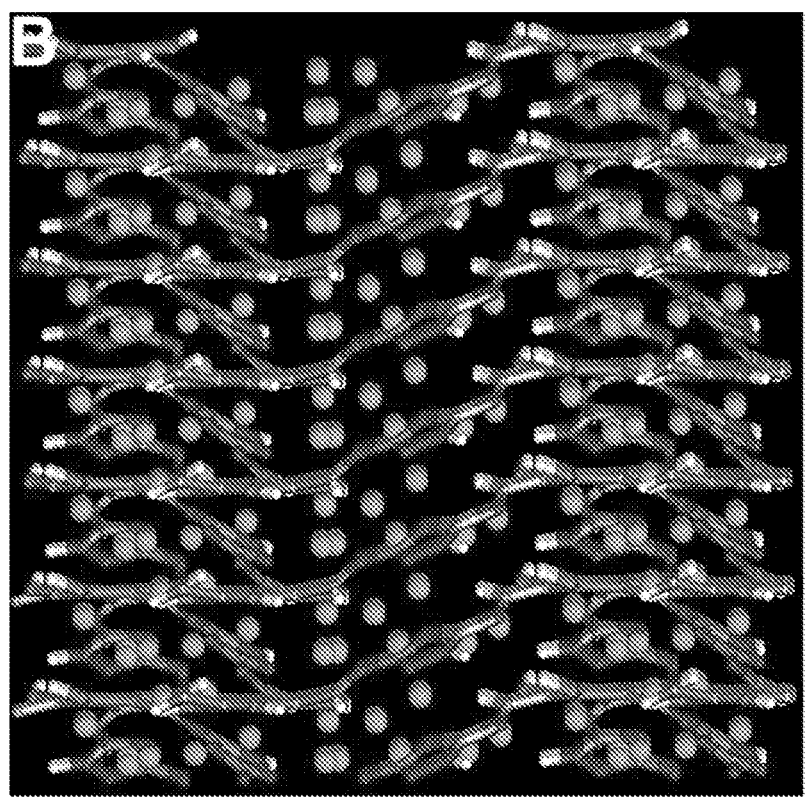
FIGS. 4B and 4C shows the two different columns of lithium that form via its interaction with phloroglucinol and triazole moieties.
Figure 4C:
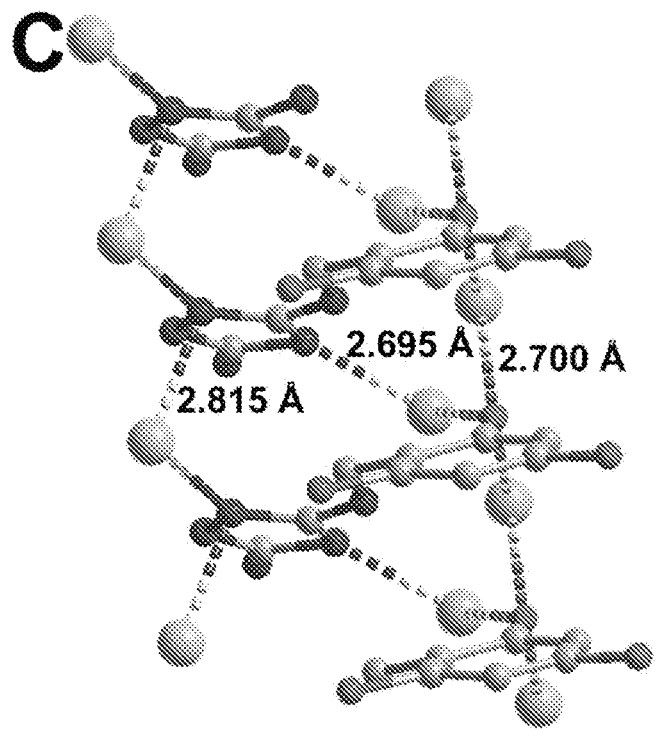

To shed some light into the structural participation of the CON towards this high and reversible lithium storage capacity, we resorted to simulations. From the observed capacity 720 mAh/g, the amount of lithium stored per formula unit of the CON was calculated to be 16. Using this as a starting composition, a 2×2×2 cell of the IISERP-CON1 was generated, and the lithium atoms were allowed to find the best probable positions using simulated annealing methods (Materials Studio V6). The resulting output was further optimized for geometry using the CASTEP routine. In the final optimized structure (relative energy: −127 eV), the lithium atoms were occupying positions close to the framework walls and resided in the interlayer space (FIG. 4A). This is significantly different from their top-on positioning found in Graphenic substrates.[32] A short contact analysis of this final structure reveal some meaningful findings when the Li atoms position around the ring nitrogens of the triazole and the hydroxyl oxygens of the phloroglucinol are considered. Two different lithium atom containing chains form, one is via the interaction of the Li atoms with the —OH and the —N atom of these groups (FIG. 4B) and the other from the interaction with only the N-atoms of the triazole (FIG. 4C). In these chains, the Li—N/Li—O separations are in the range of 2.69 to 2.8 Å, which is much longer than the Li—N/Li—O distances found in the covalently bound Lithium (~1.8-2.0 A). Interestingly, owing to the geometry of these layers the more reactive Schiff bond nitrogens are not accessible for any interaction (FIG. 4A). This perhaps explains the lack of strong interactions which could lead to irreversible Li loading. To further verify this, an experiment was carried out wherein CON was reacted with Li(OH)2 via both mechanical grinding and solution assisted process. The resulting products were analyzed using an Inductively Coupled Plasma (ICP). The analysis revealed that there was only about <2% loading of Li in both cases, which is considerably lower than the amount estimated from the measured specific capacity (16-18%). This further confirms that the CON does not have a tendency to react with Li ions via chemical bond formation, thus suggesting that bulk of the high specific capacity observed under the applied potential stems from intercalation. However, since the lithium loading was carried out without any electrochemical force, this cannot entirely exclude the formation of reactive species on the CON surface. In molecular compounds with fused aromatic rings, Li is known to form reversible, but stronger interactions, under an applied potential.

Figure 4D:
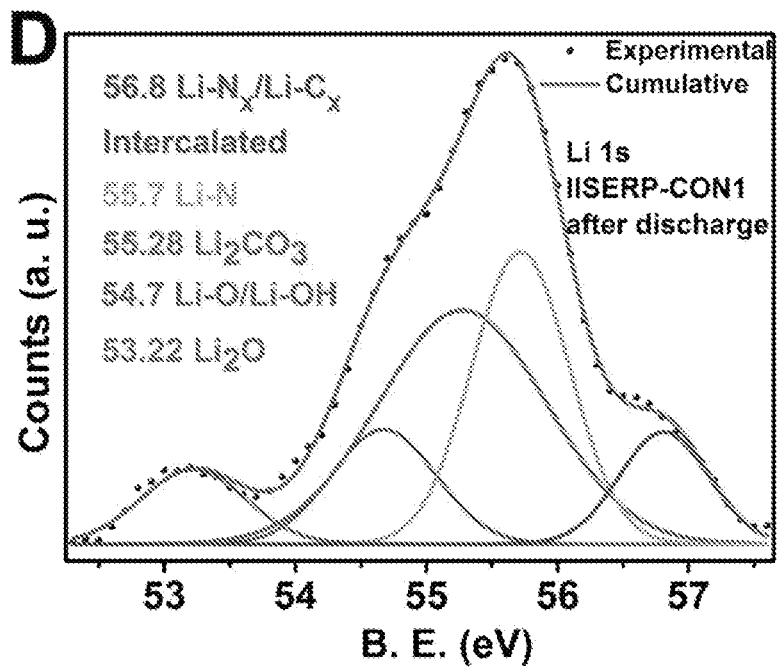
FIG. 4D shows a Li 1s XPS spectra of the post-charge-discharge (100 cycles) electrode.

To establish this, the post-discharge sample sealed under an Argon atmosphere was analysed using X-ray Photoelectron Spectroscopy (XPS), which revealed the presence of Li—N, Li—$N_x$ and Li—O/Li—OH interactions in addition to the peaks due to $Li_2CO_3$ occurring from the electrolyte contributions (FIG. 4D). This indicates the chemical affinity of the Li towards the surface groups. By considering the triazole and phloroglucinol as the binding groups (CON formula, $C_{24}N_{15}O_6H_{15}$, M. Wt. 610 g/mol), the theoretical capacity from chemically bound Li species was calculated to be 396 mAhg-1. This is higher than the value estimated from experiment (224 mAhg-1, in the potential window of 054-1.55V), but is much lower than the total experimental capacity of 774 mAhg-1 (FIG. 20). Thus from a comparison of the theoretical and the experimental capacity, the intercalation process seems to contribute about 550 mAhg-1 in the potential window of 0.01-0.54V.

Figure 4E:
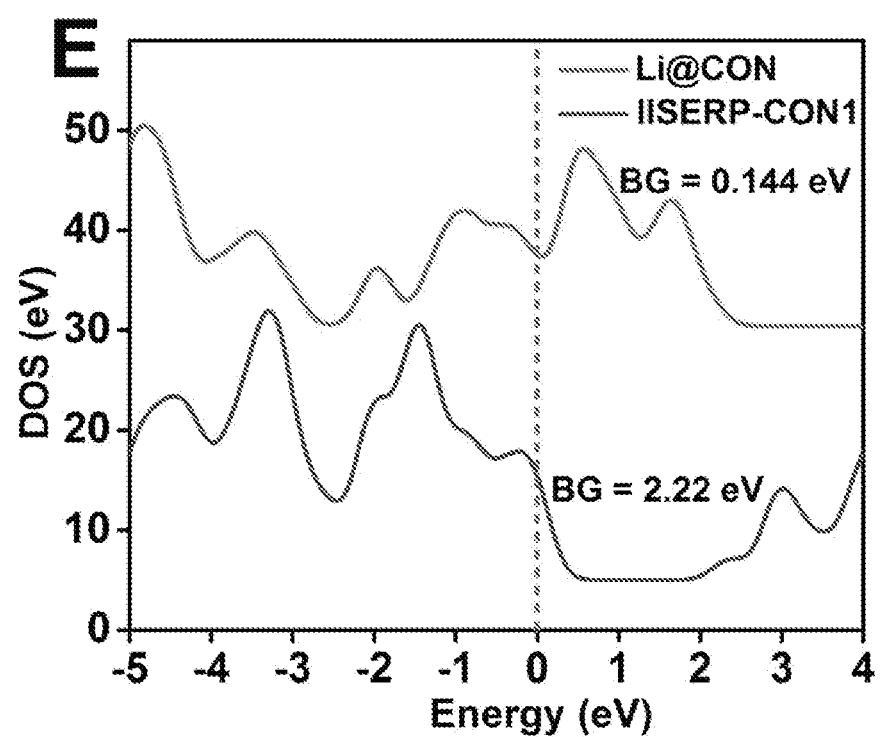
FIG. 4E shows a DOS of the CON and Li@CON calculated from periodic DFT for the CON and the Li@CON.

To gain some evidence for the electronic driving force for the lithiation, the band gap changes between the pristine COF and its lithiated form were calculated. The band gaps were calculated using the dispersion corrected DFT by employing a high plane wave basis cut-off of 500 eV and the rigorous B3LYP functional embedded in the CASTEP routine. The pristine COF has a band gap of 2.2 eV, which matches well with the experimentally determined optical band gap (2.02 eV, FIG. 21), this large band gap is expected as the framework has no extended conjugation (FIG. 4E). This agrees well with the lack of appreciable electronic conductivity in the four-probe measurements. However, upon lithiation the band gap lowers to 0.144 eV. Such lowering of the band gap, in the minimized configuration of the Li@CON, suggests the likelihood of strong electronic driving force. This is well augmented by the observations from the calculated electron density and potential map. The total electron density and the electrostatic potential as implemented in the DMol3 package of the Materials Studio was calculated. A comparison of the electrostatic potential of the pristine CON and the Li adsorbed CON shows a marked change in the e-distribution upon the Li adsorption (FIG. 22). Noticeably, due to the electrostatic interactions from the Li ions, the charge difference on the nearby carbon and nitrogen atoms has become less pronounced and the CON becomes highly activated and depletes the electrons. Clearly, the C6 rings seem to participate by transferring significant electron density towards the lithium ions. In our opinion, the calculation could be displaying the best case scenario by overestimating the electrostatics, nonetheless is pointing in the right direction.

Figure 5A:
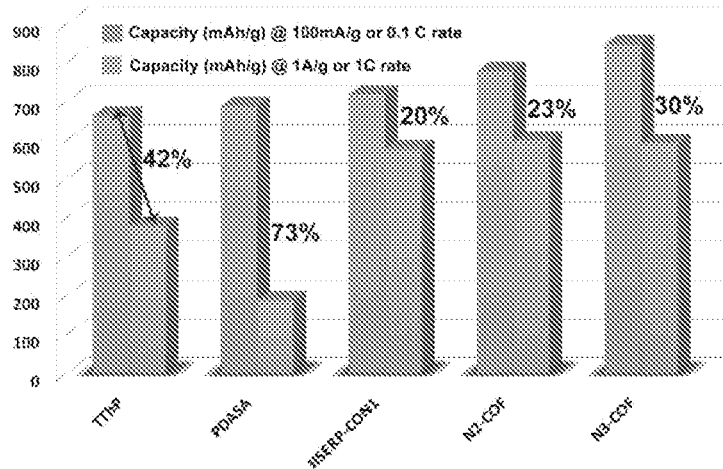
FIG. 5A shows a bar chart showing the drop in specific capacity when the current density is increased from 100 mA/g to 1 A/g in different organic framework materials with anodic character.
Figure 5B:
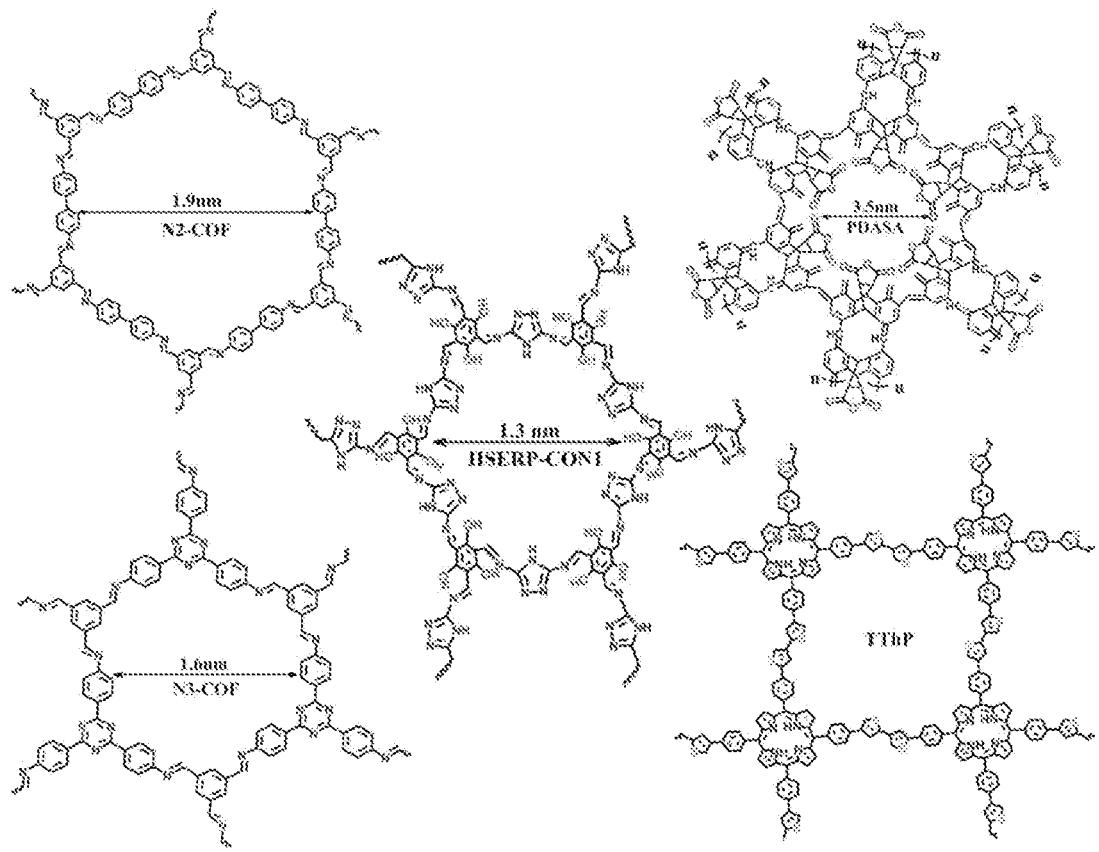
FIG. 5B shows a schematic representation of the structure of these organic frameworks showing the high and compact packing of functional groups in IISERP-CON1 giving rise to highly favorable pockets for Li interaction. Common names of COFs referred in FIG. 5: PDASA: Poly(dihydroanthracene succinic anhydride); TThP: meso-tetrakis(4-thiophenephenyl)porhyrin (TThP); IISERP-CON1: Triazole-Triformyl Phloroglucinol Based Covalent Organic Nanosheets; N2-COF: 4,4'-biphenyl-diamine and 1,3,5-Triformylbenzene derived Covalent Organic Framework; N3-COF: 2,4,6-tris(4-aminophenyl)-1,3,5-triazine and 1,3,5-triformylbenzene derived Covalent Organic Framework.

In the light of the foregoing, it is confirmed that stable performance over a wide current density window is imperative for any competing anode material. In this regard, a comparative study of specific capacities of IISERP-CON1 at the low (0.1 A/g) and the high (1 A/g) current densities with other organic materials for Li insertion-deinsertion was conducted. As can be seen from the bar chart in FIG. 5A, the drop in specific capacity in increasing the current density from 0.1 A/g to 1 A/g is about 20% in IISERP-CON1, which is the lowest among all the organic framework materials reported so far. This can be attributed to the optimal interaction between the CON and the Lithium and more importantly due to the lack of any undesirable irreversible redox activity. The structures of some of the recent self-standing organic frameworks with high capacities for Li storage are shown in FIG. 5B. When their structures are compared with that of the IISERP-CON1, evidently, IISERP-CON1 has some distinctive structural features. The electron-rich (e-donating —OH) phloroglucinol nodes are linked by the short 120o linkers derived from 3,5-diaminotriazole. This not only generates nanospaces with a high density of functional groups but also favors cooperativity between the different functionalities in assembling the Li species (FIG. 5). In comparison, the other frameworks have relatively longer linkers and the heteroatoms which serve as the active sites are far spaced. In the case of PDASA, the pores are large and the anhydride functionalities even more proximal than the functional groups in IISERP-CON1 and this reflects in higher capacity (1050 mAh/g @0.05 A/g). However, this high capacity drops by 73% compared to the 20% drop observed for IISERP-CON1. This could be due to the relatively stronger and potentially irreversible Li—COO bonds that are formed in the PDASA. Moreover, despite being short linkers, the triazoles are able to generate large enough pores in the framework which are crucial to realize smooth mass and charge transport. Meanwhile, the flexibility from the triazole enables the buckling of the layers generating highly π-stacking columnar motifs within its packing, which ensures the necessary stability required under the electrolyte solutions and the applied potential.

Thus the findings of the present invention reveal the excellent ability of these highly designable COF derived nano sheets/structures of the present invention to act as efficient electrode materials in LIBs and prompts further studies for the application of the same in other similar fields such as flexible displays, lighting devices, RFID tags, sensors, photoreceptors, gas storage and gas separation devices etc.

The following examples, which include preferred embodiments, will serve to illustrate the practice of this invention, it being understood that the particulars shown are by way of example and for purpose of illustrative discussion of preferred embodiments of the invention.

Materials and Methods:

3,5-diamino-1,2,4-triazole, 3-amino-1,2,4-triazole, Phloroglucinol were obtained from Sigma Aldrich; Hexamine and Trifluroacetic acid (TFA) were purchased from Sisco Research Laboratories. All other reagents were of analytical grade. All chemicals were used without any further purification.

Powder X-Ray Diffraction:

Powder XRDs were carried out using a full-fledge Bruker D8 Advance instrument. And the data analysis were performed using the Reflex module of the Materials Studio V6.

Thermo-Gravimetric Analysis:

Thermo-gravimetric analysis was carried out on NETSZCH TGA-DSC system. The TGAs were done under $N_2$ gas flow (20 ml/min) (purge+protective) and samples were heated from RT to 550° C. at 5K/min.

InfraRed Spectroscopy:

IR spectra were obtained using a Nicolet IDS attenuated total reflectance IR spectrometer operating at ambient temperature. The solid state IR spectra were recorded using KBr pellets as background.

Field Emission Scanning

Electron Microscope with integral charge compensator and embedded EsB and AsB detectors. Oxford X-max instruments 80 mm2 (Carl Zeiss NTS, Gmbh), Imaging conditions: 2 kV, WD=2 mm, 200 kX, Inlens detector. For SEM images, as an initial preparation, the samples were ground thoroughly, soaked in THF for 30 min. and were sonicated for 5 min. These well dispersed samples were drop casted on silicon wafer and dried under vacuum for at least 12 hrs.

Field Emission-Transmission Electron Microscopy

Transmission electron microscopy (TEM) was performed using JEM 2200FS TEM microscope operating at an accelerating voltage of 200 kV). The diffractograms were recorded at a scanning rate of 1° min-1 between 20° and 80°.

X-Ray Photoelectron Spectroscopy

X-ray source: Monochromatic Al K-alpha (Normally 75 W). Instrument: AXIS Supra, Kratos Analytical, UK. Analysis Chamber Pr<2.0×10^-7 Pa. Take-off angle: 90 deg. To obtain KINETIC ENERGY use following relation, KE(eV) =(1486.6-BE) was used. For High resolution scans Pass Energy is 20 eV, resolution ~0.5 eV. For survey scans Pass Energy is 160 eV, resolution ~2 eV.

Adsorption Study

Adsorption studies were carried out using a Micromeritics 3-FLEX pore and surface area analyser.

Electrochemical Measurements:

The constant current charge-discharge measurements were performed using MTI Battery analyzer using NEWARE software. The cyclic voltammetry and potentio-static electrochemical impedance studies were performed in Biologic VMP3 Multichannel Electrochemical Workstation equipped with ECLab software.

13C Solid-State NMR Spectroscopy:

High resolution solid-state NMR spectrum was recorded at ambient pressure on a Bruker AVANCE III 400 MHz spectrometer using a standard CP-TOSS pulse sequence (cross polarization with total suppression of sidebands) probe with 4 mm (outside diameter) zirconia rotors. Cross-polarization with TOSS was used to acquire 13C data at 100.37 MHz. The 13C ninety-degree pulse widths were 4 μs. The decoupling frequency corresponded to 72 kHz. The TOSS sample-spinning rate was 5 kHz. Recycle delays was 2 s.

Example 1

Synthesis of 1,3,5-Triformylphloroglucinol 1,3,5-Triformylphloroglucinol was synthesized following our previously reported methods[1]. 1H NMR (400 MHz, CDCl3) δ 14.10 (s, 3H, OH), 10.14 (s, 3H, CHO) ppm; 13C NMR (100.6 MHz, CDCl3) δ 192.1 (CHO), 173.6 (COH), 102.9 (CCHO) ppm.

Example 2

Synthesis of IISERP-CON1

1,3,5-triformylphloroglucinol (90 mg, 0.42 mmol) and 3,5-diaminotriazole (45 mg, 0.2 mmol) were weighed into a Pyrex tube and were dissolved in dioxane (3.0 mL), to this solution, dimethylacetamide (1.0 mL) and mesitylene (3.0 mL) were added and stirred until a greenish yellow color was observed. Following this, 1.0 mL of aqueous acetic acid (6 M solution) was added. Then the Pyrex tube was flash frozen in a liquid nitrogen bath and sealed. The Pyrex tube along with its contents was placed in an oven at 120° C. for 3 days. This yielded about 110 mg of reddish brown coloured solid which was washed with hot DMF, dioxane, MeOH, acetone and THF (81%, isolated yield). This reddish brown solid was subjected to a Soxhlet extraction using DMF/methanol as solvent. Importantly, no color was found in the wash solution, suggesting lack of any unreacted materials or small oligomers, which was further confirmed from a solution NMR of the final wash solution. (Formula for IISERP-CON1: $C_{24}N_{15}O_6H_{15}$, M. Wt. 610 g/mol, CHNO Obsd. C=48.9; H=3.20; N=36.45; O=16.90. Calc. 82.36; H=4.84; N=12.81%). Note the significant deviation between the observed and the calculated CHNO values. This discrepancy can be explained by the presence of significant amounts of terminal aldehyde and amine functionalities being present in the CON. This is confirmed by the 13C-SSNMR and IR (see figures S1 and S8). From this CHN analyses mismatch it can be estimated that there is about 8% of such terminal CHO and NH2 functionalities, which indicates that the polycondensation is not too high in the CONs.

Example 3

Synthesis of Monomer 3-amino-1,2,4-triazole (1.42 g, 0.017 mole) was dissolved in a hot mixture of ethanol (40 mL) and a solution of 1,3,5-Triformylphloroglucinol (1.26 g, 0.006 mole) in ethanol was slowly added to it. The resulting mixture was refluxed and the dirty white precipitate of the monomer was collected. The precipitate of monomer was washed with copious amounts of hot ethanol and dried under reduced pressure. Finally the monomer was crystallized from a hot solution of DMF by slow evaporation. Tiny crystal were formed which were not suitable for single crystal X-ray diffraction. The crystals were highly soluble in DMSO. So the monomer was characterized by liquid state NMR and solid state IR studies.

Example 4

Coin Cell Preparation for Electrochemical Measurements

IISERP-CON1 was activated by heating at 150° C. under vacuum for 24 hrs. 75% of CON, 25% Super-P carbon & 10% PTFE binder were mixed by grinding thoroughly in a dry and clean mortar-pestle. NMP was added drop by drop to make a highly viscous slurry. The slurry was coated on a copper foil to make an electrode containing the nanosheets. It was placed in a vacuum oven at 120° C. for 24 hrs. The CON coating on the copper foil (electrode) remained non-leachable to this drying procedure and no visible cracks appeared. Thus coated electrodes were cut in accordance to the size of 2032 coin cell. This aptly cut electrodes were again dried under vacuum at 80° C. before taking into the glove box. Then coin cells were prepared inside the glovebox. LiPF6 dissolved in 1:1 ethylene carbonate and dimethyl carbonate was employed as the electrolyte and about 2% (v/v) of fluoro ethylene glycol solvent was added to prevent the formation of the solid electrolyte interphase after the 1st discharge cycle.

Note: From the charge-discharge set-up the Open Circuit Voltage of the coin cells were determined to be ~3V.
Remark: In all electrochemical measurements the potential has been measured with respect to $Li/Li^+$ half cell.

Example 5

Computational Details

All calculations were performed using the different modules implemented in the Materials Studio V6.

The Monte-Carlo methods were used to obtain the most probable locations of the Li species within the low-energy configuration of the COF. These were carried out using the Simulated Annealing techniques available within the Materials Studio V.6.0. Default parameters were utilized. Automatic temperature control and 100000 cycles/cell was employed to optimize the structure. Universal force filed (UFF) in conjugation with a QEq charge equilibration method was employed for the geometry optimization, however, it was noticed that applying the equilibration (QEq) did not make much of a difference to the final configurations. No constraints were placed during the optimizations.

For the geometry optimization of the periodic COF structure, tight-binding Density Functional Theory was employed. The PBE exchange-correlation functional and parameters from the Slater-Koster library were used with a plane wave basis set cut-off of 340 eV. All calculations were spin polarized and only the Γ-point was sampled. UFF-based Lennard-Jones dispersion corrections were included in Energy, Force and Displacement calculations and the cell was optimized. A smearing parameter of 0.005 Ha was applied.

To establish the room temperature stability of the lithiated CON a CASTEP dynamics calculation employing a NVE ensemble at 298K was carried out. For the MD simulations, the CASTEP Dynamics module of the Materials Studio was used. For the calculations a 1×1×2 cell was used and the gradient-corrected exchange correlation were applied using the Generalized Gradient Approximation (GGA) and Perdew-Burke-Ernzerhof (PBE) functional. The Newtonian equations of motions (NPT) were chosen for defining the ensemble considering its suitability in optimization of periodic 2D structure. Ultrasoft pseudopotentials with a plane wave basis cut-off of 260 eV were employed. And, a DFT-D based semi-empirical dispersion correction was applied in the optimization. Electronic minimization was carried out using the Density Mixing functional. Excellent convergence was achieved for all electronic levels and with no noticeable systematic shifts in energy. Tolerance used: 1×e-006.

The band structures were calculated the geometry optimized configurations (lowest energy configuration from the DFTB) using the CASTEP built within the MS package. For these, a Norm-conserving pseudopotentials with a plane wave basis cut-off of 500 eV was employed and the B3LYP functional was used. Electronic minimizations were achieved using an All Bands/EDFT algorithm. All calculations were performed on the unit cell and separately on a 2×2×2 super cell.

For the calculation of the electron density and the electrostatic potentials DMol3 implemented in the Materials Studio was employed. For the calculations a 2×2×2 cell was used and the gradient-corrected exchange correlation were applied using the Generalized Gradient Approximation (GGA) and Perdew-Wang 91 (PW91) functional. A DFT-D correction was applied, a Global scheme was used for the orbital cut-off (5.1 Ang.) with a SCF tolerance of 1×e-006. And a smearing parameter of 0.005 Ha was applied.

We claim:

1. Self-exfoliated covalent organic framework derived nanosheets (CONs) comprising a plurality of 3,5-diaminotriazole units and a plurality of triformyl phloroglucinol units, in an extended layered covalent framework wherein, the triazole based diamine units are bonded to the triformyl phloroglucinol units via Schiff bonds to generate a porous structure.

2. The covalent organic nanosheets as claimed in claim 1, wherein the covalent organic nanosheet has the structure of Formula I, and forms channels with pores having dimensions of 1.4 nm×1.7 nm.

3. The covalent organic nanosheets as claimed in claim 1, wherein, the covalent organic nanosheets are characterized by BET surface area in the range of about 507 $m^2/g$; pore volume of about 0.37 cc/g; N2 uptake 77K (~220 cc/g); and thermal stability over 300° C.

4. The covalent organic nanosheets as claimed in claim 1, wherein, the covalent organic nanosheets exhibit thermal and chemical stability towards different solvents, electrolytes, and acidic media.

5. The covalent organic nanosheets as claimed in claim 1, wherein, the covalent organic nanosheets are prepared by a) reacting triformyl phloroglucinol with 3,5-diaminotriazole in dioxane in the presence of dimethylacetamide and mesitylene under stirring; b) adding 6M aqueous acetic acid followed by flash freezing the reaction mass in a liquid nitrogen bath; and c) heating the mixture at a temperature of 120° C. for a sufficient period of time followed by cooling to obtain the covalent organic nanosheets.

6. The covalent organic nanosheets as claimed in claim 1, wherein, the covalent organic nanosheet exhibits specific capacity of ~720 mAh/g at a current density of 100 mA/g, when used as an anode in a Li-ion battery.

7. The covalent organic nanosheets as claimed in claim 6, wherein, the covalent organic nanosheets are reusable as an anode for more than 100 cycles with no loss of specific capacity.

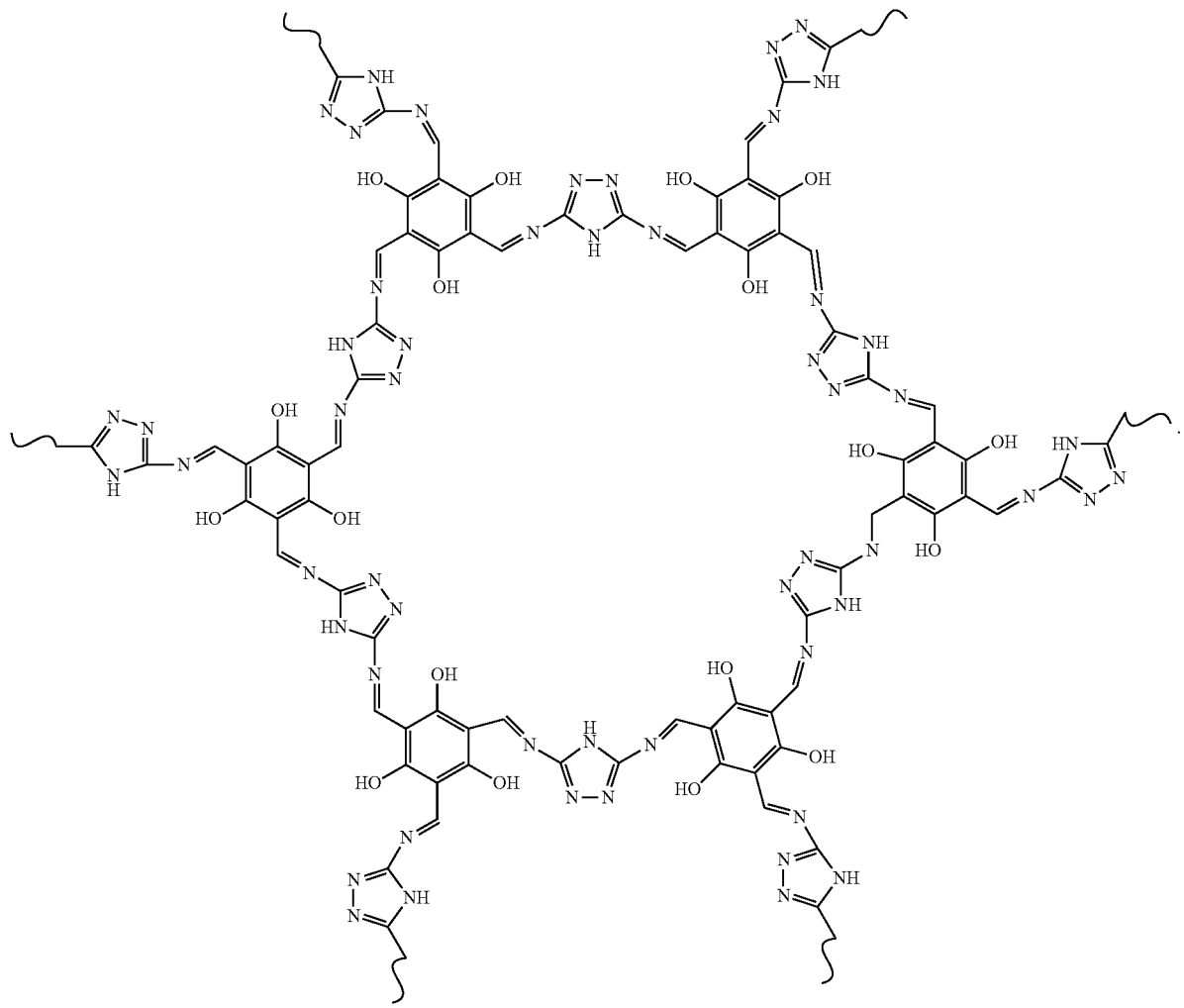

8. A device comprising covalent organic framework derived nanosheets (CONs) of claim 1.

9. The device as claimed in claim 8, wherein, the device is selected from the group consisting of solar cells, batteries and capacitors.

10. The device as claimed in claim 9, wherein, the device is a lithium ion battery.

* * * * *